United States Patent
Snow et al.

(10) Patent No.: US 9,600,001 B2
(45) Date of Patent: Mar. 21, 2017

(54) DEVICES, SYSTEMS AND METHODS FOR PURGING AND LOADING SORBENT TUBES

(75) Inventors: Miles Snow, Newmarket (CA); Lee Marotta, North Bergren, NJ (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 688 days.

(21) Appl. No.: 13/349,859

(22) Filed: Jan. 13, 2012

(65) Prior Publication Data
US 2013/0180315 A1 Jul. 18, 2013

(51) Int. Cl.
G05D 22/02 (2006.01)
G01N 25/56 (2006.01)
G01N 33/00 (2006.01)

(52) U.S. Cl.
CPC ............. *G05D 22/02* (2013.01); *G01N 25/56* (2013.01); *G01N 33/0016* (2013.01)

(58) Field of Classification Search
CPC .......... B01D 53/22; B01D 2259/40003; B01D 2259/402; B01D 53/04; B01D 53/0446; B01D 53/0454; B01D 53/261; G01N 33/0011; G01N 1/2214
USPC ........... 73/23.41, 23.42, 29.01, 25.04, 29.02, 73/29.05, 24.04, 335.02, 335.06
See application file for complete search history.

(56) References Cited

U.S. PATENT DOCUMENTS

| 3,944,400 | A | | 3/1976 | Bird |
| 4,247,311 | A | * | 1/1981 | Seibert ............... B01D 53/0446 96/111 |
| 4,612,019 | A | | 9/1986 | Langhorst |
| 5,123,277 | A | * | 6/1992 | Gray et al. .................... 73/29.01 |
| 5,656,928 | A | * | 8/1997 | Suzuki et al. ................ 324/71.1 |
| 5,847,291 | A | | 12/1998 | Green |
| 7,600,439 | B1 | * | 10/2009 | Patterson et al. .......... 73/863.21 |
| 2011/0017061 | A1 | * | 1/2011 | Carlsson ............................ 95/18 |

FOREIGN PATENT DOCUMENTS

| GB | 2439948 A | 1/2008 |
| WO | 2010001178 A1 | 1/2011 |

OTHER PUBLICATIONS

ESSR for EP 13735588 mailed on Apr. 1, 2016.

* cited by examiner

*Primary Examiner* — Daniel S Larkin
*Assistant Examiner* — Jamar Ray
(74) *Attorney, Agent, or Firm* — Rhodes IP PLC; Christopher R Rhodes

(57) ABSTRACT

Certain embodiments described herein are directed to devices that can be used in purging and loading applications. In some examples, a device configured to purge a sorbent tube until a desired water level is reached is provided. In other examples, a device configured to load a sorbent tube with a desired water level is provided. Systems and methods using the devices are also described.

16 Claims, 19 Drawing Sheets

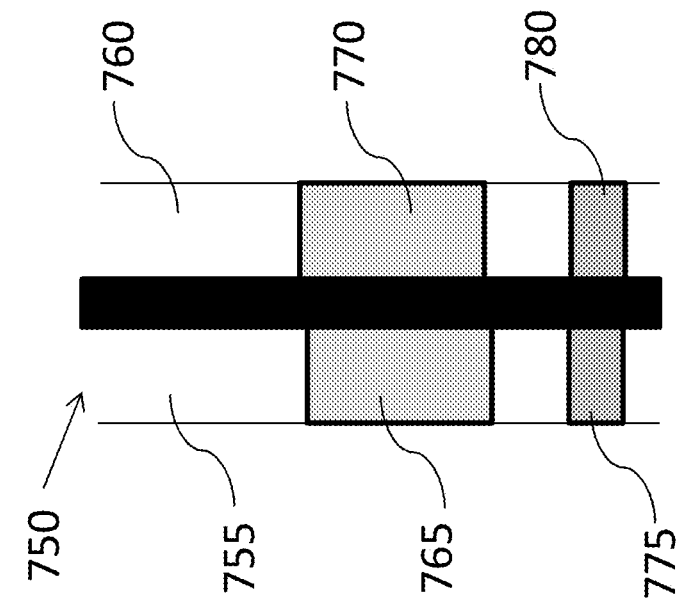
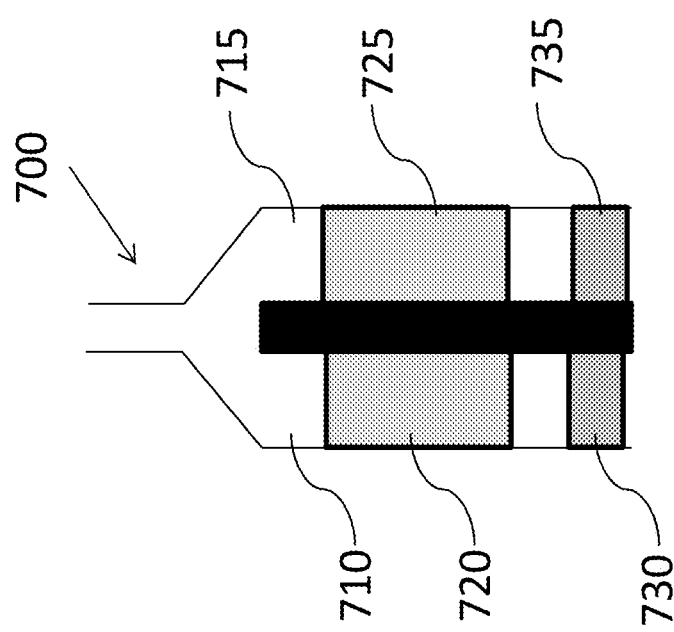
FIG. 7B
FIG. 7A

DEVICES, SYSTEMS AND METHODS FOR PURGING AND LOADING SORBENT TUBES

TECHNOLOGICAL FIELD

Certain features, aspects and embodiments are directed to devices that can be used in purging and loading applications. In particular, certain embodiments described herein are directed to devices, systems and methods that can be used to reduce water within a sorbent tube to a desired level prior to sampling.

SUMMARY

In a first aspect, a device comprising a humidity sensor constructed and arranged to fluidically couple to a sorbent tube, the humidity sensor configured to receive a fluid stream from the sorbent tube to determine the level of water in the sorbent tube is provided.

In certain embodiments, the humidity sensor can be configured to detect an inflection point as an indicator of a desired level of water in the sorbent tube. In some embodiments, the device comprising the humidity sensor can be configured to receive the sorbent tube. In other embodiments, the device comprising the humidity sensor can be configured to fluidically couple to a separate receptacle comprising the sorbent tube. In some examples, the device can include a plurality of receptacles each configured to receive a single sorbent tube. In other examples, the device can include a plurality of humidity sensors in which each of the plurality of receptacles can be fluidically coupled to one of the plurality of humidity sensors. In certain examples, the device can include a temperature sensor. In some embodiments, the device can include a switching valve fluidically coupled to the device. In additional embodiments, the device can include a purging gas source coupled to the switching valve.

In other embodiments, the device can include a humidity sensor electrically coupled to a processor. In some examples, the processor can be configured to stop flow of purging gas from the purging gas source to the sorbent tube when the humidity sensor detects a water level in the received fluid stream below a selected water level. In other examples, the selected water level can be 3% relative humidity or less. In some embodiments, the switching valve can be actuated by the processor to stop flow of the purging gas to the sorbent tube when the humidity sensor detects a water level in the received fluid stream below a selected water level. In certain embodiments, fluid flow from the purging gas source can be stopped by the processor to stop flow of the purging gas to the sorbent tube when the humidity sensor detects a water level in the received fluid stream below a selected water level. In other examples, the device can include a temperature sensor and a processor, in which the processor is electrically coupled to the humidity sensor and to the temperature sensor, the processor configured to calculate the water level in the fluid stream received by the humidity sensor using a humidity signal from the humidity sensor and a temperature signal from the temperature sensor.

In another aspect, a device comprising an inlet fluidically coupled to a plurality of receptacles each configured to receive at least one sorbent tube, the device further comprising an outlet fluidically coupled to at least one humidity sensor configured to receive a fluid stream from at least one of the plurality of receptacles to determine the level of water in a sorbent tube in the receptacle providing the fluid stream to the humidity sensor is described.

In certain examples, the device can include at least one temperature sensor coupled to the device. In other examples, the device can include an inlet and an outlet for each of the plurality of receptacles. In some embodiments, the device can include a switching valve fluidically coupled to the outlets of the receptacles. In further embodiments, the switching valve can be configured to provide fluidic coupling between a single receptacle and the humidity sensor. In additional embodiments, the switching valve is configured to provide fluidic coupling between two receptacles and the humidity sensor. In some examples, the device comprises a switching valve in each of the outlets of the plurality of receptacles. In further examples, the device can include a switching valve in each of the inlets of the plurality of receptacles. In certain embodiments, the device comprises a plurality of humidity sensors each fluidically coupled to a single receptacle of the plurality of receptacles. In other embodiments, each of the plurality of humidity sensors can be electrically coupled to a processor. In some embodiments, at least one of the plurality of receptacles can be configured to receive two sorbent tubes. In further embodiments, at least two receptacles of the plurality of receptacles have different dimensions. In some examples, at least one receptacle comprises an inlet size smaller than an inlet size of another receptacle in the plurality of receptacles. In certain examples, the device further comprises an inlet and an outlet for each of the plurality of receptacles, at least one humidity sensor fluidically coupled to each of the plurality of receptacles, and at least one temperature sensor in at least one outlet of the plurality of receptacles. In some examples, the device can include a plurality of humidity sensors each fluidically coupled to a single receptacle of the plurality of receptacles.

In an additional aspect, a sorbent tube comprising a body for receiving a sorbent material, the body comprising a first end and a second end opposite the first end, the second end of the body configured to receive a humidity sensor configured to detect water in the sorbent tube is disclosed.

In certain embodiments, the humidity sensor can be integral with the second end of the body of the sorbent tube. In additional embodiments, the sorbent tube can include an electrical coupler configured to electrically couple the humidity sensor to a processor. In some embodiments, the sorbent tube can include at least one coupler on the first end of the sorbent tube, the coupler configured to fluidically couple the sorbent tube to a purging gas source. In other embodiments, the sorbent tube can include a first sorbent material and a second sorbent material in the body between the first end and the second end. In some embodiments, a first type of sorbent material is present and comprises a weaker sorbent strength than a second type of sorbent material that is present. In certain examples, the first type of sorbent material can be positioned adjacent the first end of the body. In other examples, the second end of the body can be further configured to couple to a temperature sensor. In additional examples, the sorbent tube can include a heat shielding material in the second end of the sorbent tube. In some examples, the sorbent tube can include a switching valve in one of the first end and the second end.

In another aspect, a system comprising a purging gas source comprising a coupler configured to provide fluidic coupling between one end of a sorbent tube and the purging gas source, and a humidity sensor configured to couple to another end of the sorbent tube and to receive fluid from the sorbent tube to detect water levels in the received fluid is provided.

In certain examples, the system can include a receptacle configured to receive the sorbent tube and to couple to the purging gas source and to fluidically couple to the humidity sensor. In some examples, the system can include a manifold fluidically coupled to the purging source, the manifold comprising a plurality of outlets each configured to fluidically couple to a sorbent tube. In other examples, the system can include a processor electrically coupled to the humidity sensor. In certain embodiments, the system can include a manifold fluidically coupled to the humidity sensor, in which each port of the manifold is also fluidically coupled to a single sorbent tube. In some embodiments, the system can include a plurality of humidity sensors each configured to fluidically couple to a single sorbent tube. In additional embodiments, the system can include a manifold fluidically coupled to the purging gas source, the manifold comprising a plurality of outlets each configured to fluidically couple to a sorbent tube. In some examples, the system can include at least one temperature sensor coupled to the system. In further examples, the system can include a manifold fluidically coupled to the humidity sensor, in which each port of the manifold is also fluidically coupled to a single sorbent tube. In additional examples, the system can include a processor electrically coupled to the plurality of humidity sensors and the temperature sensor.

In another aspect, a system comprising purging gas source, a receptacle configured to receive at least one sorbent tube and fluidically coupled to the purging gas source, and a humidity sensor fluidically coupled to the receptacle and configured to receive fluid from the receptacle to detect water levels in the received fluid is described.

In certain embodiments, the purging gas source can be coupled to a plurality of receptacles each configured to receive at least one sorbent tube. In other embodiments, the receptacle can be configured to receive two parallel sorbent tubes. In further embodiments, the receptacle can be configured to receive two sorbent tubes in series. In some embodiments, the system can include a manifold fluidically coupled to the purging source, the manifold comprising at least one outlet configured to fluidically couple to the receptacle. In other examples, the system can include a processor electrically coupled to the humidity sensor. In further examples, the system can include a manifold fluidically coupled to the humidity sensor, in which each port of the manifold is also fluidically coupled to a single sorbent tube. In additional examples, the system can include a plurality of humidity sensors each configured to fluidically couple to a single sorbent tube. In certain examples, the system can include a processor electrically coupled to each of the plurality of humidity sensors. In other examples, the system can include a temperature sensor electrically coupled to the processor.

In an additional aspect, a method comprising purging a sorbent tube with a purging gas, detecting a humidity level of fluid exiting the purged sorbent tube with a humidity sensor fluidically coupled to the sorbent tube, and discontinuing purging of the sorbent tube when the humidity level drops below a selected humidity level is disclosed.

In certain embodiments, the method comprises detecting a temperature of the exiting fluid using a temperature sensor. In some embodiments, the method comprises detecting a humidity level change during a first period of about 0.01% humidity per second or less. In other embodiments, the method comprises detecting a humidity level change during a second period of about 0.1% humidity per second. In additional embodiments, the method comprises detecting a humidity level change during a third period of about 0.01% humidity per second or less after the detected change during the second period and discontinuing purging of the sorbent tube when the change during the third period is detected. In some examples, the method comprises discontinuing purging of the sorbent tube when the detected water level is about 3% relative humidity or less. In certain examples, the method comprises actuating a valve between the sorbent tube and a purging gas source that provides the purging gas to control flow of purging gas to the sorbent tube. In additional examples, the method comprises actuating the valve to the closed position when the detected humidity level drops below a selected humidity level. In some embodiments, the method includes continuously monitoring the detected humidity levels in the exiting fluid. In additional embodiments, the method includes discretely monitoring the detected humidity levels in the exiting fluid. In some examples, the method includes simultaneously purging a plurality of sorbent tubes with the purging gas. In further examples, the method includes using a single humidity sensor to monitor the humidity levels in each of the plurality of sorbent tubes. In some embodiments, the method includes using a plurality of humidity sensors each fluidically coupled to a single sorbent tube to monitor the humidity level in each of the plurality of sorbent tubes. In some examples, the method includes addressing each of the plurality of humidity sensors. In additional examples, the method includes using at least one temperature sensor fluidically coupled to fluid exiting at least one sorbent tube to determine the humidity level.

In another aspect, a method of purging water from a sorbent tube comprising introducing a purging gas into a sorbent tube, detecting a water level in fluid exiting the sorbent tube with a humidity sensor fluidically coupled to the sorbent tube, and stopping introduction of the purging gas into the sorbent tube when the detected water level in the exiting fluid is below a selected level is provided.

In certain examples, the selected level is configured to be about 3% relative humidity or less. In other examples, the method includes actuating a valve between the purging gas source and the sorbent tube to a closed position when the detected water level in the exiting fluid is below the selected level. In additional examples, the method includes switching off a gas source providing the purging gas when the detected water level in the exiting fluid is below the selected level. In further examples, the method includes simultaneously providing the purging gas to a plurality of sorbent tubes.

In an additional aspect, a method of facilitating removal of water from a sorbent tube, the method comprising providing a humidity sensor configured to detect water levels in a fluid exiting the sorbent tube and provided to the humidity sensor is disclosed.

In certain examples, the method comprises discontinuing provision of a purging gas to the sorbent tube when the humidity sensor detects a water level in the fluid exiting the sorbent tube below a selected level. In additional examples, the method comprises providing a valve configured to be placed between a purging gas source and the sorbent tube, the valve configured to permit flow of purging gas to the sorbent tube in one state and prevent flow of purging gas to the sorbent tube in another state. In other examples, the method comprises providing a processor configured to electrically couple to the humidity sensor. In further examples, the method comprises providing a gas manifold configured to provide fluidic coupling between the sorbent tube and a purging gas source. In some examples, the method comprises providing a receptacle configured to receive the sorbent tube and provide fluidic coupling between a purging gas source and the sorbent tube. In additional examples, the method comprises providing a plurality of humidity sensors each configured to fluidically couple to a single sorbent tube to detect water levels in the fluidically coupled sorbent tube. In certain examples, the method comprises providing a plurality of receptacles each configured to receive at least one sorbent tube, in which each of the plurality of receptacles is fluidically coupled to one of the plurality of humidity sensors. In some examples, the method comprises providing a temperature sensor. In other examples, the method comprises providing an instrument configured to couple to the sorbent tube and to detect species eluting from the sorbent tube.

In another aspect, a kit comprising a sorbent tube and a humidity sensor is disclosed. In certain examples, the humidity sensor can be configured to detect water levels in fluid exiting the sorbent tube. In other examples, the kit can include a temperature sensor. In certain embodiments, the kit can include a gas manifold configured to couple the sorbent tube to a purging gas source. In some embodiments, the kit can include a receptacle configured to receive the sorbent tube. In additional embodiments, the kit can include a plurality of receptacles each configured to receive at least one sorbent tube. In other embodiments, the kit can include a plurality of humidity sensors. In some examples, the kit can include a plurality of sorbent tubes. In further examples, the kit can include providing instructions for using the plurality of humidity sensors to purge the plurality of sorbent tubes of water. In some examples, the kit can include instructions for using the humidity sensor to purge the sorbent tube of water.

Additional features, aspects and examples are described in more detail below.

BRIEF DESCRIPTION OF THE FIGURES

Certain illustrative embodiments are described in more detail below with reference to the accompanying figures in which:

FIG. 7A is an illustration of a receptacle with a common fluid flow path and FIG. 7B is an illustration of a receptacle with separated fluid flow paths, in accordance with certain examples;

Figure 1:
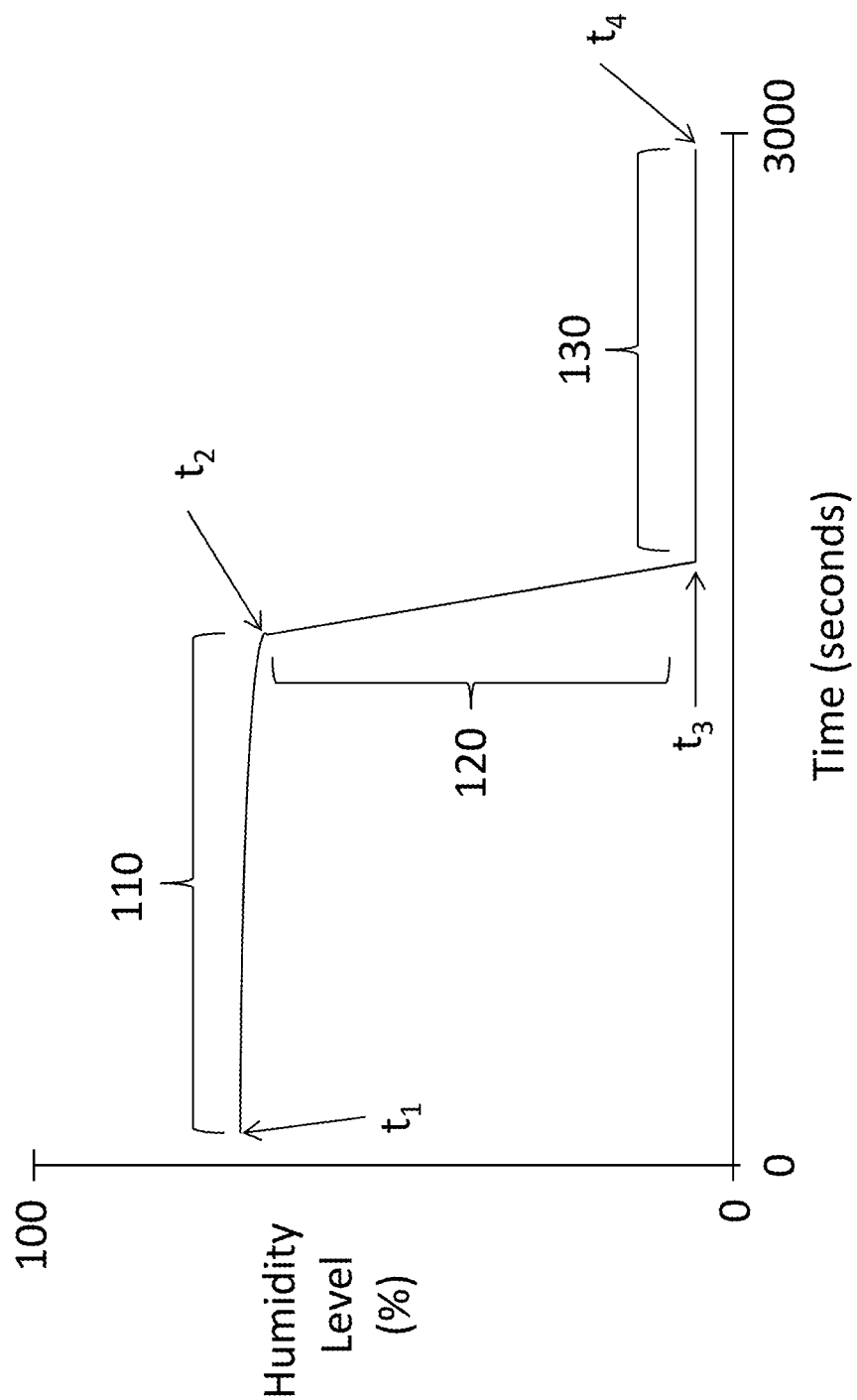
FIG. 1 graphically illustrates detection of humidity levels in a sorbent tube, in accordance with certain examples.

It will be recognized by the person of ordinary skill in the art, given the benefit of this disclosure, that the relative positions and sizes of the components in the figures are not limiting and that no particular size, dimension, thickness or arrangement is implied as being required based on the representations of the components shown in the figures.

DETAILED DESCRIPTION

In the illustrative embodiments described below, certain components are included in the devices and systems. Depending on the desired configuration of the device, it may be desirable to include additional components, omit one or more components or rearrange or substitute other components into the devices and systems.

In certain embodiments, the devices, systems and methods described herein can be used to purge sorbent tubes of adsorbed water or to load tubes with a desired amount of water. Purging can be performed prior loading the tube with sorbent material, after loading the tube with sorbent material but before exposure of the sorbent tube to analyte, after loading the tube with sorbent material and after exposure of the sorbent tube to analyte but before analysis of the analyte, or at other times. While the terms "purge" and "purging" are used in certain instances herein, these terms are not intended to mean that all water is removed from the tube. Instead, purging can be performed until a desired level of water is achieved, which may be substantially zero or can be some other selected water level if desired. In some examples, the devices, systems and methods provided herein can be used to load the sorbent material of the sorbent tube with a desired level of water prior to exposure of the sorbent tube to one or more analytes. By loading the tube with a desired amount of water, the tube can be tuned or used as a filter to prevent or reduce adsorption of certain species that may be present in a sample, e.g., polar species. Additional uses of the devices, systems and methods disclosed herein are provided in more detail below.

Thermal desorption (TD) is commonly used for the determination of trace organics in air, when using in conjunction with gas chromatography/or mass spectrometry or combinations thereof. The technique can concentrate these analytes many orders of magnitude but also concentrates water as well. The water levels can be as high as 35 mg loading on a standard thermal desorption tube also referred to herein in certain instances as a sorbent tube. This water can affect both the chromatography of the analytes as well as suppress responses. In order to reduce the effect of water, it is possible to either dry purge the tube or use alternate sampling strategies such as passing the sample through a Nafion® dryer. The Nafion® dryer can be effective at removing water but can also remove polar compounds as well. The principle of dry purging is to pass carrier gas in the sampling direction to remove water from hydrophobic sorbents such as the Carbon Molecular Sieves (CMS). It is difficult, however to predict how much water is on the sorbent tube. As such, purging of the tubes is usually done for excessive times to ensure all water has been removed. Drawbacks exist to excessive purging including the loss of ultra volatile gases that may be present as well as increased and unnecessary analytical time due to the excessive purging.

In certain embodiments, the devices and systems described herein can use reduced levels of purging gases to provide a desired level of water in a sorbent tube. In some embodiments, purging may be automatically halted or stopped once the water level reaches a desired level. Such automatic halting or stopping can be performed, for example, by discontinuing provision of a purging gas to a sorbent tube once or as soon as the desired water level is detected. In other embodiments, the devices and systems described herein can be used to load a sorbent tube with a desired amount of water. As discussed elsewhere herein, loading of the sorbent tube with certain levels of water can provide for tuning of the sorbent tube to prevent (or reduce) substantial adsorption of certain species by the sorbent material in the tube.

In certain embodiments, the systems, devices and methods disclosed herein can be used to reduce levels of water in a sorbent tube at ambient temperature, e.g., about 23-25° C., at a temperature above ambient temperature or at a temperature below ambient temperature. In some examples, a correction factor can be used to account for any variations in humidity measurements with temperature. Such correction factor can be based on the actual temperature used to purge the tubes, e.g., as detected with an internal or external temperature sensor or thermometer. In some instances, the system can include a heater, cooler or both such that temperature is fixed and any calibration of the humidity sensor can be based on the operating temperature of the system. If desired, the temperature of the purging gas can be controlled or matched to the temperature of the system such that purging gas flows with a different temperature do not alter the humidity measurements. In some embodiments, only the sorbent tube to be purged can be heated or cooled, whereas in other embodiments, the entire apparatus that hold the sorbent tube may be exposed to heat or cooling. If desired, the system can be heated or cooled for a desired period so that temperature equilibration may occur prior to any humidity measurements. In some examples, the system can be configured to implement a delay time prior to initiation of humidity measurement and/or introduction of a purging gas such that the sorbent tube can reach the desired temperature.

In certain examples, FIG. 1 graphically illustrates a humidity response of a sorbent tube as a function of time. In a typical purging operation, a gas is introduced into the sorbent tube. In some examples, the gas may be an inert gas such as, for example, nitrogen, hydrogen, helium, argon, dry air, carbon dioxide or other gases that generally would not react with analyte to any substantial degree under the analytical conditions. Illustrative flow rates for the purging gas (or the loading gas in instances where the gas is used to add water to a sorbent tube) can vary from about 10 mL/minute to about 500 mL/minute, e.g., about 100-200 mL/minute. The flow rate of the gas can vary depending on the nature of the gas, and different flow rates can result in shifting of the detected humidity levels, e.g., shifting of the curve of FIG. 1 left or right. The particular pressure selected can also vary, and the pressure selected desirably retains higher gas capacity to remove any water from the sorbent tube.

As shown in FIG. 1, an unpurged tube generally has high levels of water adsorbed to the sorbent material. The particular water level can vary from tube to tube and can be, for example, 35 mg or more or, in other instances, can be less than 35 mg of water, e.g., 10 mg, 5 mg or a few mg of water. As purging gas is introduced into the sorbent tube, water desorbs from or diffuses out of the sorbent material and becomes entrained in the purging gas. The purging gas comprising the water exits the sorbent tube where it can be detected with a humidity sensor or other suitable sensor including electrochemical sensors and electrodes. As shown in FIG. 1, during a first period 110, the humidity level remains substantially constant. In mathematical terms for the time between $t_1$ and $t_2$, $$\frac{d[\text{humidity level}]}{dt} \approx 0 \text{ for } t_1 \text{ through } t_2$$

for the first period 110. In some instances, the slope, e.g., change in humidity level, may be negative 0.01% humidity per second or less between times $t_1$ and $t_2$. As purging gas flows through the sorbent tube, at time $t_2$ a rapid decrease in the humidity level is observed during the period 120. In mathematical terms for successive periodic intervals within $t_2$ and $t_3$ of the second period 120, $$\frac{d[\text{humidity level}]}{dt} \neq 0 \text{ for } t_2 \text{ through } t_3$$

with the slope during the period 120 being substantially negative. In certain examples, the absolute magnitude of the slope between periods $t_2$ and $t_3$ may be substantially larger, e.g., 10× greater, than the slope between times $t_1$ and $t_2$. For example, the slope between times $t_2$ and $t_3$ may be −0.1% humidity per second or higher in absolute magnitude, e.g., −0.2% humidity per second or more. At time $t_3$, substantially all water has been purged from the sorbent tube and the change in humidity levels from time $t_3$ to time $t_4$ is about zero as little or no amounts of water remain in the sorbent tube. The change in slope during a third period 130 from time $t_3$ to $t_4$ may be similar to that observed during the first period 110, e.g., the slope may be −0.01% humidity per second. In certain embodiments of the devices and systems described herein, the detection of the large change in slope magnitude, e.g., the slope change during the period 120, can be used to determine when purging is complete. For example, detection of a large change in slope followed by little or no change in slope can be used to determine when purging is substantially complete. In some instances, subsequent detection of substantially no change in slope followed by detection of a large slope change can be used as an indicator or inflection point of substantially complete purging of the sorbent tube. In certain embodiments, once the large slope change is observed, purging may be discontinued as soon as the change in slope approaches about zero, e.g., at the beginning of the period 130 at time $t_3$.

In other instances, purging of the sorbent tube may be considered complete when the humidity level drops below a desired level. In such configurations, continuous monitoring of the purging may or may not be implemented. Instead, once the measured humidity drops below a selected level, then purging of the sorbent tube may be considered complete. In instances where the desired level of humidity is used to determine when purging is complete, purging may be monitored at periodic or discrete intervals. For example, humidity levels may be continuously monitored subsequent to introduction of a purging gas, humidity levels may be monitored after a delay period, e.g., 500 seconds or more, humidity levels may be monitored incrementally or other monitoring times and intervals can be selected. In some embodiments, where a single humidity sensor is used with a plurality of sorbent tubes, it may be desirable to monitor each sorbent tube incrementally such that humidity levels for all tubes can be measured using the single humidity sensor.

Figure 2A:
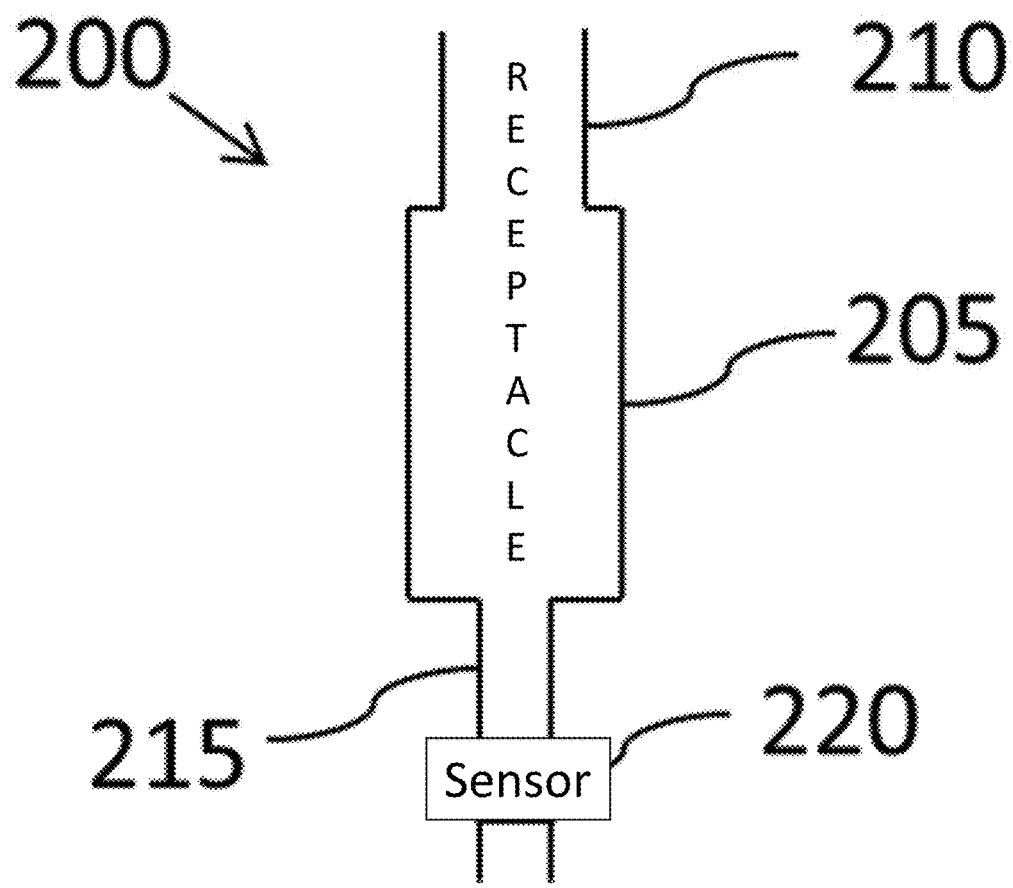
FIGS. 2A and 2B are illustrations of devices comprising a humidity sensor for detecting humidity levels, in accordance with certain examples.

In certain embodiments, a device suitable for detecting humidity levels is shown in FIG. 2A. The device 200 comprises a receptacle 205 configured to receive a sorbent tube. The receptacle 205 is generally sized and arranged to receive a sorbent tube and may have dimensions larger than the sorbent tube to ensure the entire sorbent tube can be placed in the receptacle 205. In some embodiments, a friction fit may exist between the sorbent tube and the receptacle 205 such that purging gas is forced through the sorbent tube to exit the receptacle 205. In other instances, a gasket may exist such that purging gas is forced through the sorbent tube to exit the receptacle 205. In other instances, purging gas can be provided to the receptacle 205 and can enter the sorbent tube 205 and other portions of the receptacle 205. The device 200 also comprises a fluid conduit or connection 210 to permit coupling of the receptacle 205 to a fluid line that provides a purging gas. A humidity sensor 220 can be positioned downstream of the receptacle 205 (FIG. 2A) in a fluid outlet 215 of the receptacle 205 so that the fluid stream exiting the sorbent tube in the receptacle 205 is provided to the humidity sensor 220 for detection of the water levels in the fluid stream.

Figure 2B:
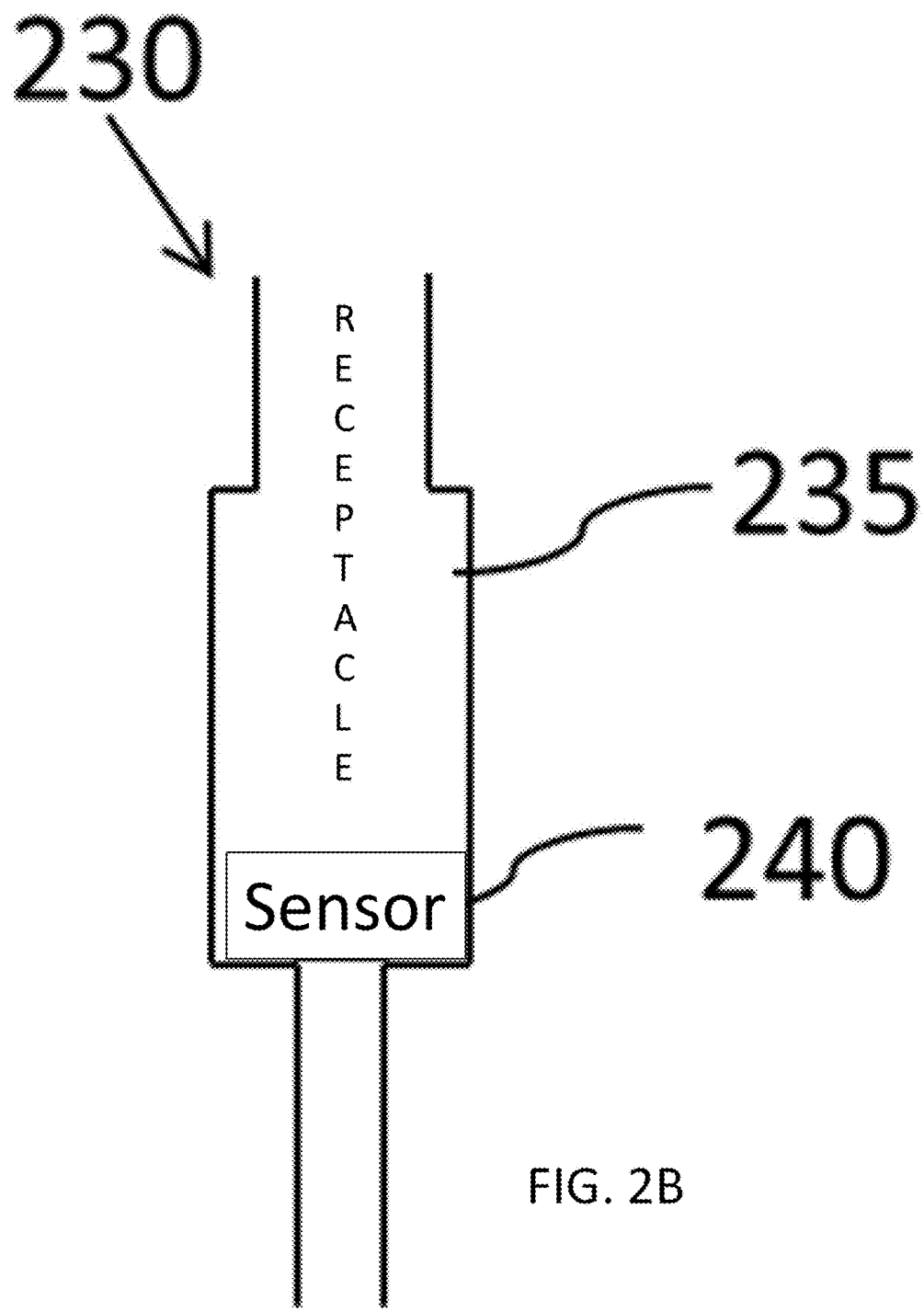
Figure 2C:
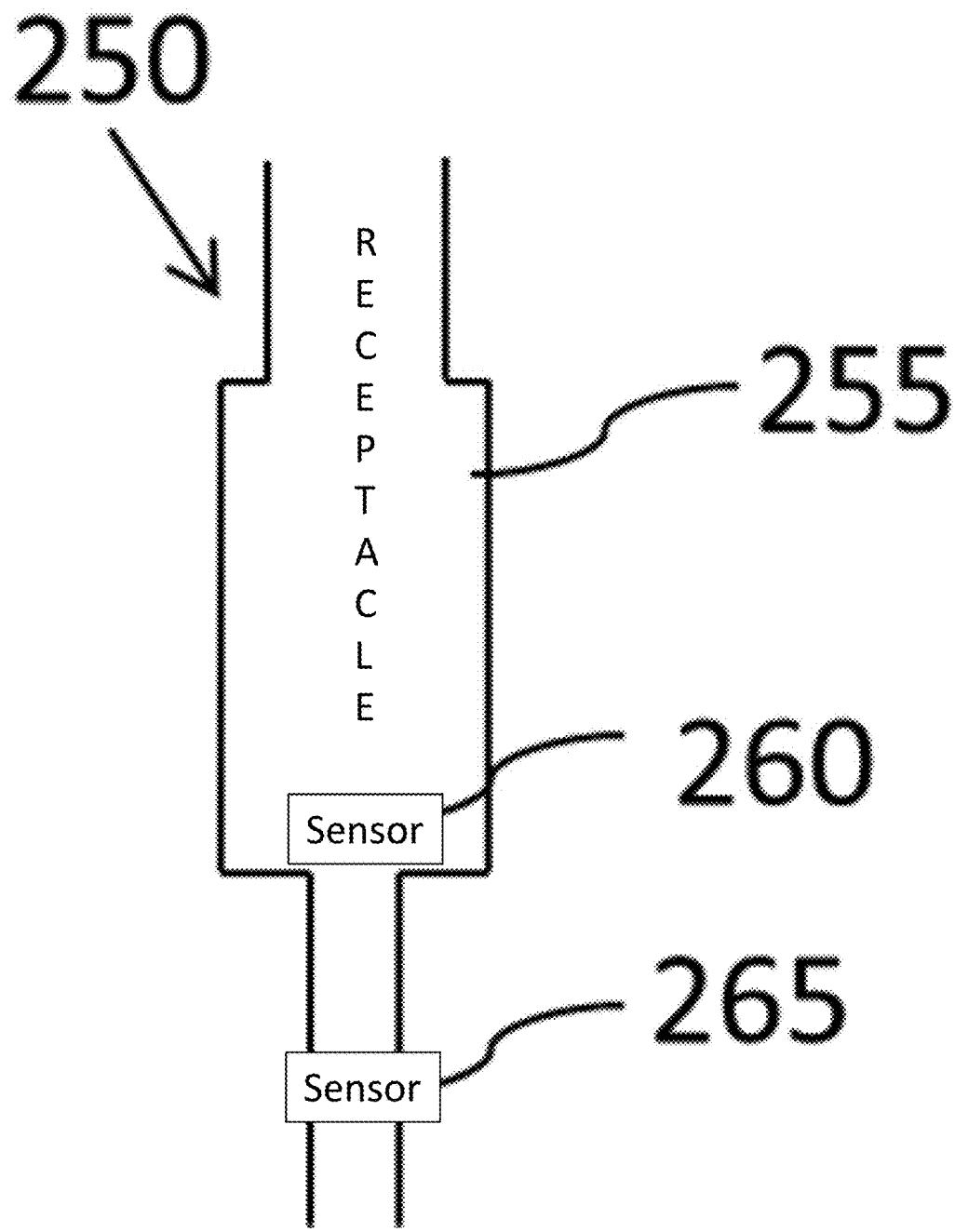
FIG. 2C is an illustration of a device comprising two humidity sensors, in accordance with certain examples.

In certain embodiments, the humidity sensor can be positioned at other areas relative to the positioning of the sorbent tube in the receptacle. For example and referring to FIG. 2B, a device 230 comprising a humidity sensor 240 positioned in a receptacle 235 is shown. Referring to FIG. 2C, a device 250 comprising a first humidity sensor 260 in a receptacle 255 and a second humidity sensor 265 in a fluid outlet of the receptacle 255 is shown. The use of more than a single humidity sensor can provide for increased accuracy. In addition, where two or more humidity sensors are present, the humidity sensors can be the same or can be different. For example, it may be desirable to select a first humidity sensor having a fast response time but low sensitivity to determine initial humidity levels. The second humidity sensor can be selected to be more accurate than the first humidity sensor and used to determine more precise levels of water in the sorbent material. More than two humidity sensors can also be present in the devices and systems described herein. Optionally, one or more temperature sensors (not shown) can be present in the devices 200, 230 and 250 to compensate for humidity level deviations due to changes in temperature. Where a temperature sensor is present, it may be present upstream of the humidity sensor or downstream of the humidity sensor. In some examples, the temperature sensor is adjacent to the humidity sensor to ensure the two sensors are at about the same temperature. In some embodiments, the humidity sensor can be included or integrated into its own receptacle or container which can be fluidically coupled with the receptacle comprising the sorbent tube.

Figure 3A:
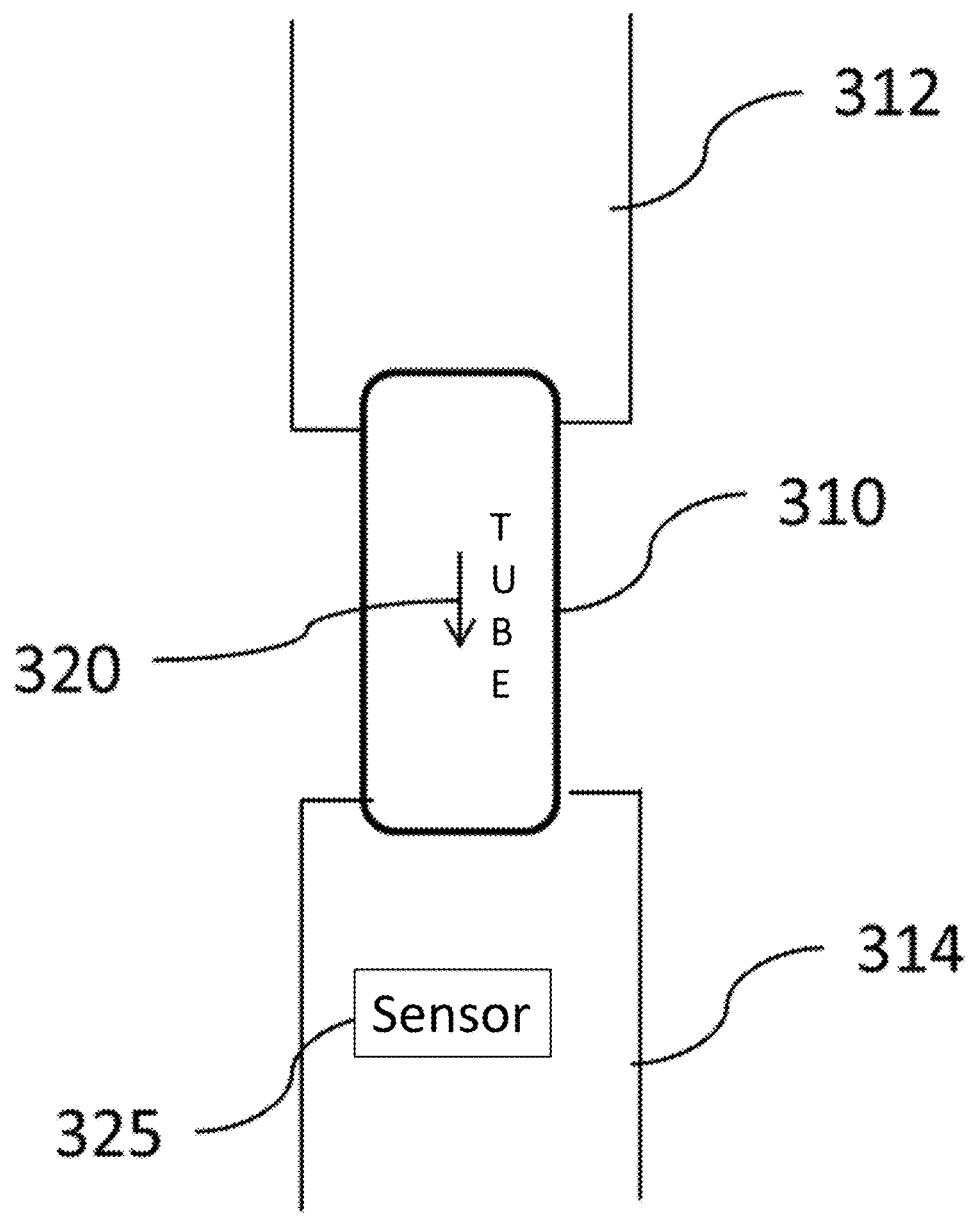
FIGS. 3A and 3B are illustrations of a device comprising a humidity sensor that is fluidically coupled to a sorbent tube, in accordance with certain examples.

In certain examples, the devices and systems described herein may omit a receptacle entirely and may be configured to couple directly to the ends of the sorbent tube. For example and referring to FIG. 3A, a sorbent tube 310 is shown as being fluidically coupled to a humidity sensor 315 through a fluid conduit 314. The sorbent tube 310 is fluidically coupled to a source of purging gas through a fluid conduit 312. While fluid conduits 312 and 314 are shown as being at opposite ends of the sorbent tube 310 and generally in-line with the sorbent tube 310, one or more of the fluid conduits can be positioned at a right angle to the sorbent tube 310 or at another desired angle. Generally, the fluid conduits 312, 314 may be coupled to the sorbent tube 310 in any desired orientation that permits fluid to flow to and from the sorbent tube 310. Each of the fluid conduits 312 and 314 may include a gasket or suitable fittings to provide a substantially fluid tight seal between the conduits 312 and 314 and the ends of the sorbent tube 310. In operation, a purging gas is provided through the fluid conduit 312, flows through the sorbent tube 310 in the direction of arrow 320 and exits the sorbent tube 310 into the fluid conduit 312. As shown in FIG. 3A, a humidity sensor 325 is positioned in the fluid conduit 314 and is operative to detect water levels in the fluid stream that exits the sorbent tube 310. In addition, one or more temperature sensors may also be present in one or more of the fluid conduits 312 and 314 or in the sorbent tube 310 to provide for increased accuracy in the humidity level measurements.

Figure 3B:
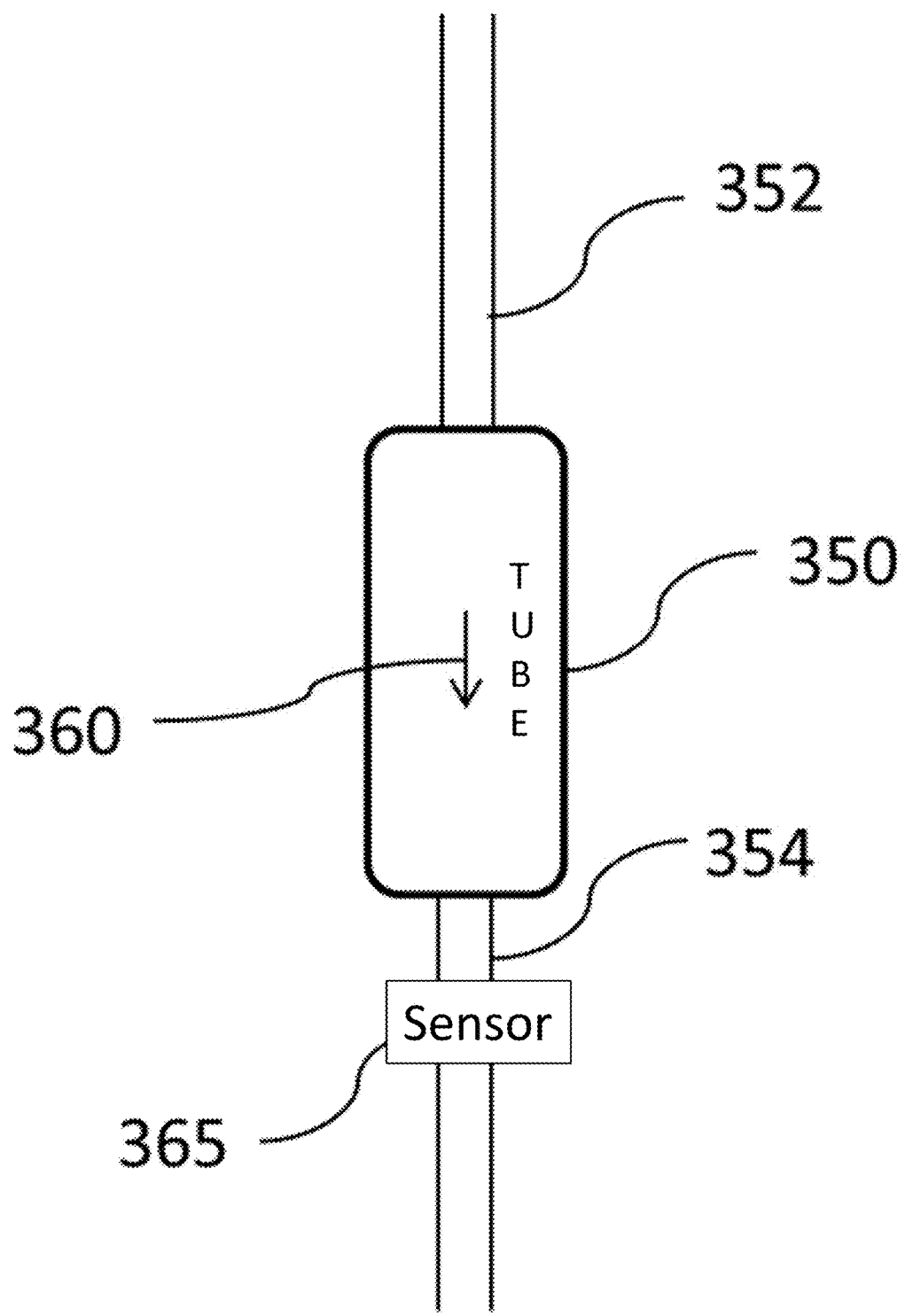

In certain embodiments, the purging gas may be provided to the fluid flow path within a sorbent tube. For example, the sorbent tube can include integral couplings or fittings to provide fluid flow from a purging gas source into the internal fluid flow path of the sorbent tube. An illustration is shown in FIG. 3B. The sorbent tube 350 comprises a first fitting 352 and a second fitting 354 on an opposite end of the sorbent tube 350. A purging gas can be provided from a gas source (not shown) to the first fitting 352 of the sorbent tube 350. As purging gas flows through the internal fluid flow path of the sorbent tube 350, adsorbed water desorbs and diffuses into the purging gas as it flows in the general direction of arrow 360. Purging gas with water exits the sorbent tube 350 through the second fitting 354 where water levels can be detected by a humidity sensor 365 in the second fitting 354. If desired, the humidity sensor 365 can be positioned external to the sorbent tube 350, e.g., in a fluid flow line that is fluidically coupled to the second fitting 354. In addition, one or more temperature sensors (not shown) can be present in the sorbent tube 350 or in a fluid line fluidically coupled to the sorbent tube 350. Where sensors are present in the sorbent tube 350, they can be added prior to disposal of sorbent material in the sorbent tube or after disposal of sorbent material in the sorbent tube. Where the sorbent material disposal operation is performed at a temperature that may harm the sensor(s), the sensor is desirably added to the sorbent tube after disposal of the sorbent material to the sorbent tube. In embodiments where a humidity sensor is integral to the sorbent tube, the sorbent tube can include one or more external connectors such that a lead, plug or other device can be electrically coupled to the external connectors to provide electrical coupling between the integral sensor and another desired device or system, e.g., a display, printer, recorder, processor or the like.

Figure 4A:
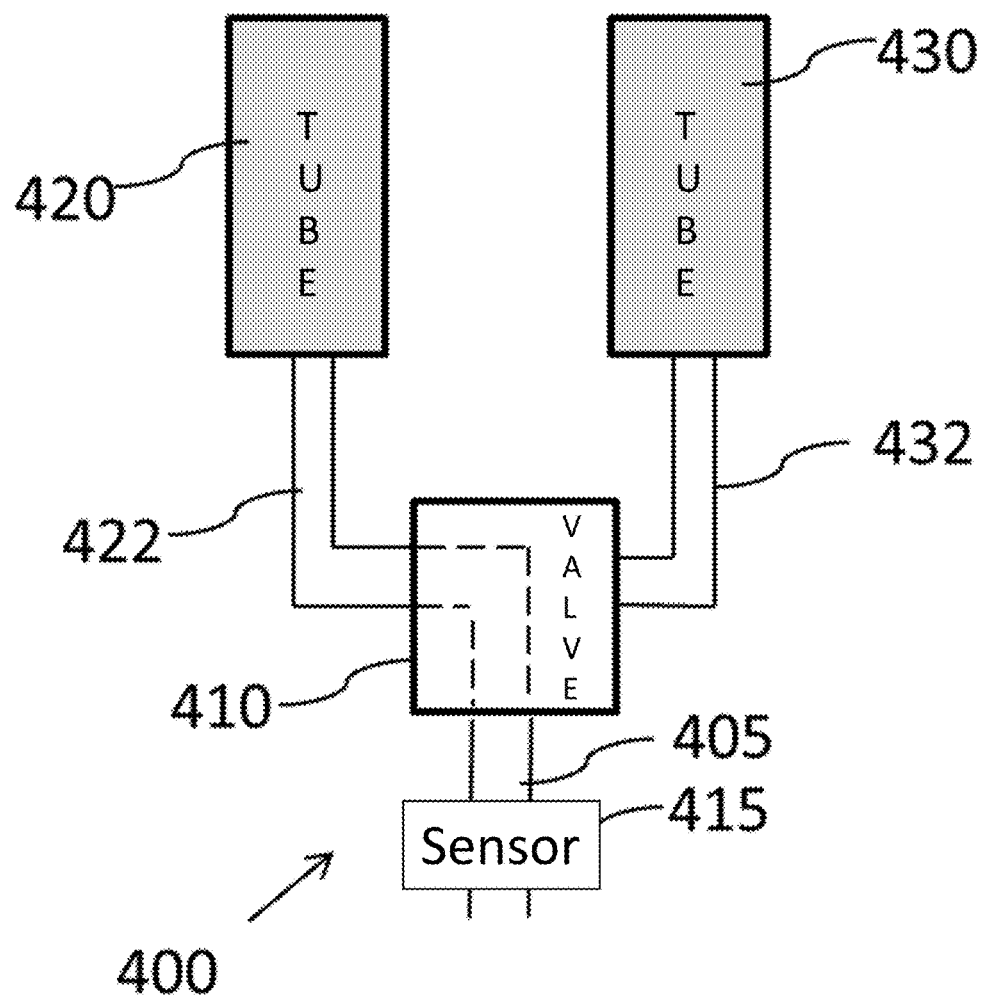
FIGS. 4A and 4B are illustrations showing two sorbent tubes fluidically coupled to a humidity sensor through a valve, in accordance with certain examples.
Figure 4B:
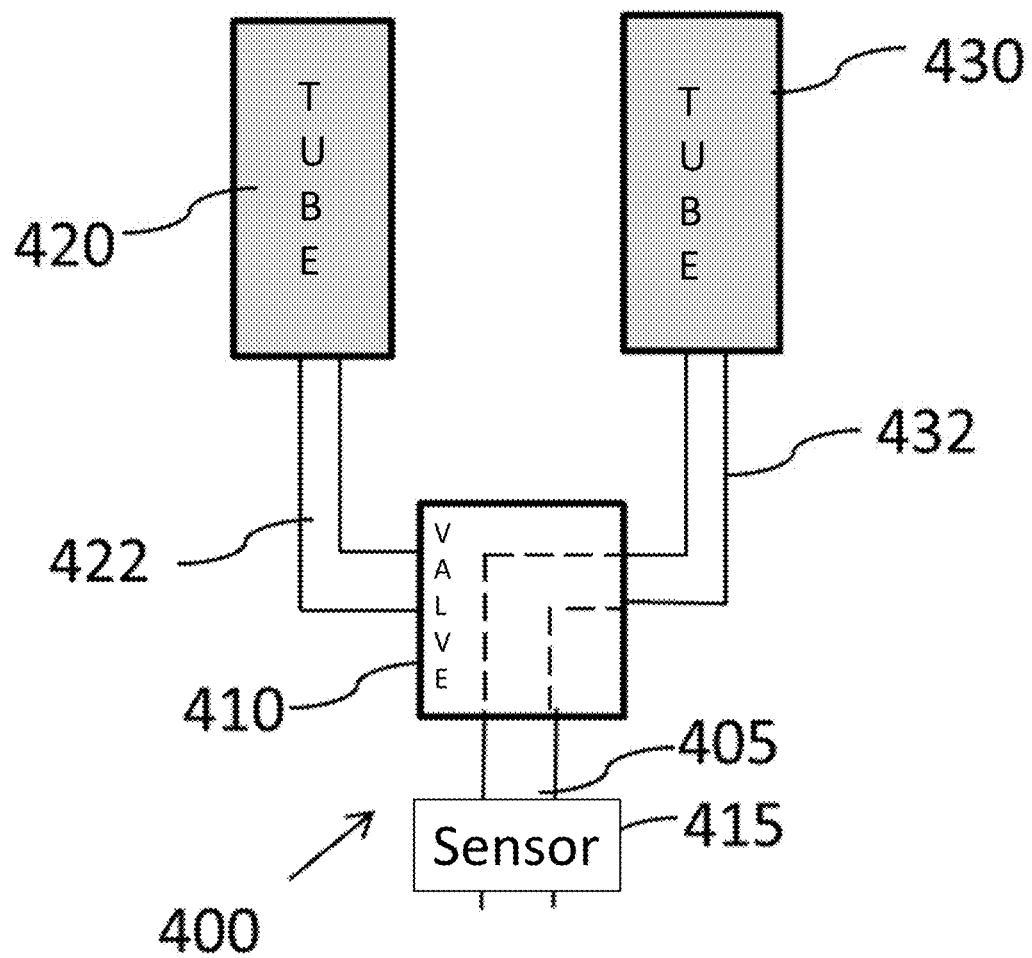

In certain examples, a single humidity sensor can be used with more than a single sorbent tube. For example, to reduce overall cost and to add simplicity to the device, a single humidity sensor can be present and operative to receive fluid flow from two or more sorbent tubes. Illustrations are shown in FIGS. 4A and 4B. The device 400 comprises a fluid flow path 405 fluidically coupled to a valve 410. The fluid flow path 405 comprises a humidity sensor 415 operative to detect water levels in fluid. Two sorbent tubes 420 and 430 are each fluidically coupled to the valve 410 through fluid flow paths 422 and 432, respectively. The valve 410 is configured with an internal fluid flow path that can be switched to provide fluidic coupling between the sorbent tube 420 and the humidity sensor 415 (FIG. 4A) or the sorbent tube 430 and the humidity sensor 415 (FIG. 4B). The valve 410 may be cycled with a frequency of about 0.1 Hz to about 10 Hz. Where more than two sorbent tubes are used with a single humidity sensor, the valve can be configured to provide sequential fluidic coupling between the various sorbent tubes and the single humidity sensor. The valve 410 can be a low cost solenoid valve or other suitable valve that can be switched to fluidically couple two fluid flow paths. In a typical operation, the valve 410 would be switched to provide fluidic coupling between the sorbent tube 420 and the humidity sensor 415 for a desired period, e.g., 1-10 or 1-100 seconds or more, as shown in FIG. 4A. Levels of water in the fluid stream received from the sorbent tube 420 would be detected and used as an indicator of the water level in the sorbent tube 420. The valve 410 would then be switched to its second position to provide fluidic coupling between the sorbent tube 430 and the humidity sensor 415 for a desired period, e.g., 1-10 or 1-100 seconds or more, as shown in FIG. 4B. Levels of water in the fluid stream received from the sorbent tube 430 would be detected and used as an indicator of the water level in the sorbent tube 430. In one alternative mode of operation, the humidity sensor 415 can be fluidically coupled to the sorbent tube 420 until the sorbent tube 420 reaches a desired water level. The valve 410 can then be switched to provide fluidic coupling between the sorbent tube 430 and the humidity sensor 415 to permit detection of water levels in the sorbent tube 430. If desired, the provision of purging gas to the sorbent tube 430 can be delayed for a desired period. In some examples, upstream of the sorbent tubes 420 and 430 may be a gas manifold or gas fittings (not shown) which can provide fluidic coupling between the sorbents tube 420 and 430 and a purging gas source. In measuring fluid streams from the sorbent tube 420 and 430, the humidity levels can be measured using the same channel (or displayed as being overlapping on a single display or printer) and when the measurements substantially overlap at a desired level, purging may be discontinued. Alternatively, fluid flow from each sorbent tube may be provided to its own discrete detector (or channel thereof) such that humidity levels in the sorbent tubes can be displayed or monitored independently of each other.

In certain examples, the valve 410 can be a solenoid valve or other inexpensive valve that can be switched at a desired frequency and provide fluidic coupling (or not depending on the state of the valve) between two or more components of the device. In some examples, the valve 410 can be configured as a three-way valve or a multi-way valve so that a single valve can provide fluidic coupling between a plurality of sorbent tubes and a single humidity sensor. Similarly, a multi-way valve can be positioned upstream of a plurality of sorbent tubes so that purging gas can be selectively provided to one or more sorbent tubes but not necessarily all sorbent tubes at the same time. Depending on the flow rates used, a swafer device commercially available from PerkinElmer Health Sciences, Inc. (Waltham, Mass.) can be used to provide purging gas to a desired sorbent tube and/or to provide a fluid stream from a selected sorbent tube to a humidity sensor. Illustrative swafer devices are described in more detail in commonly owned pending U.S. patent application Ser. No. 12/472,948, the entire disclosure of which is hereby incorporated herein by reference for all purposes. In some examples, the valve 410 can be omitted entirely and fluid exiting from both the sorbent tube 420 and the sorbent tube 430 can be provided simultaneously to the humidity sensor 415. In such a configuration, the overall signal is representative of average humidity levels in the two sorbent tubes.

Figure 5:
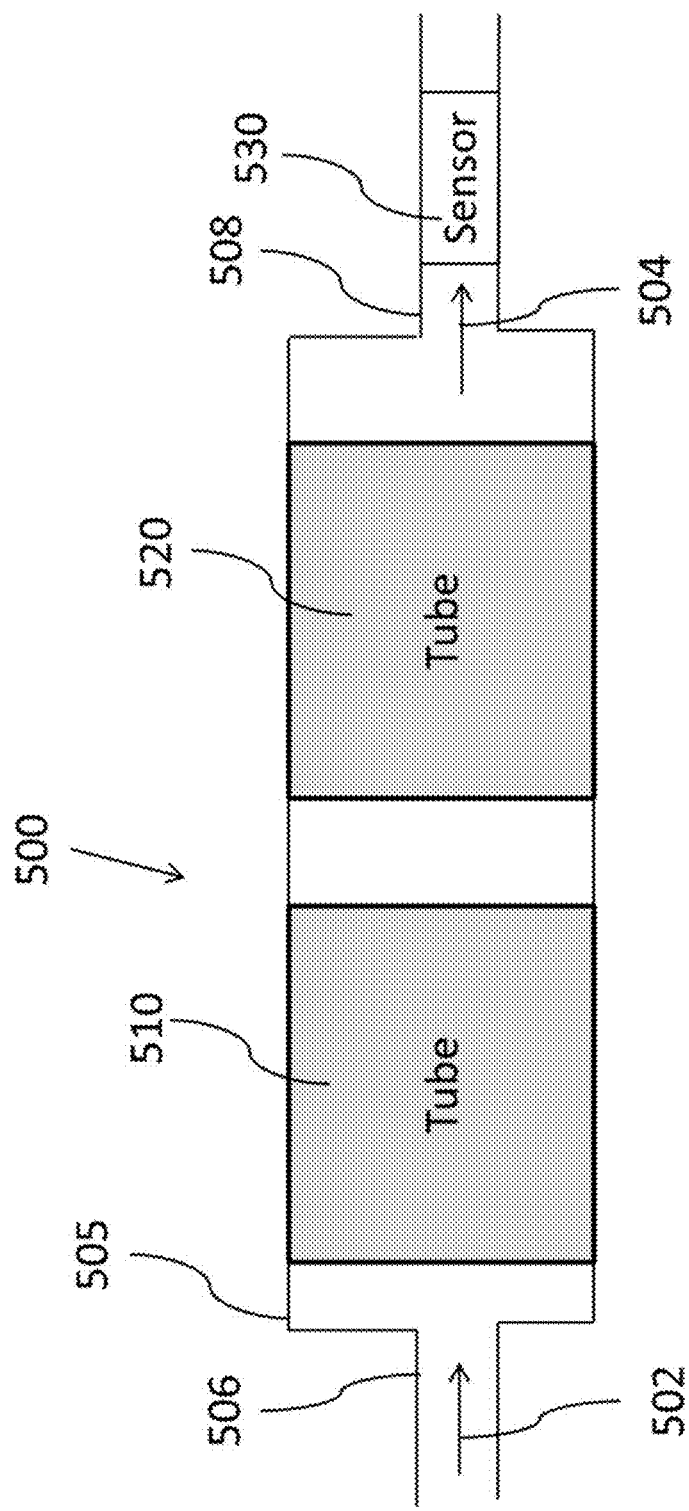
FIG. 5 is an illustration of a receptacle configured to receive two sorbent tubes in series, in accordance with certain examples.

In certain embodiments, two or more sorbent tubes can be placed in-line to purge each of them. An in-line configuration may be desirable for example to purge the sorbent tubes prior to exposure to any analyte. An illustration of a device comprising in-line sorbent tubes is shown in FIG. 5. A device 500 comprises a receptacle 505 sized and arranged to receive two sorbent tubes 510 and 520. The receptacle 505 can be fluidically coupled to a purging gas source (not shown) at an end 506 and to a humidity sensor 530 at an end 508. The humidity sensor 530 is operative to detect water levels in fluid exiting the receptacle 505. A purging gas is provided in the direction of arrow 502, and fluid exits the receptacle 505 in the direction of the arrow 504. Such fluid typically includes water from both the sorbent tubes 510 and 520. Where the tubes 510 and 520 are in-line as shown in FIG. 5, water can exit the tube 510 and may become re-adsorbed to the tube 520. Once substantially all water exits the tube 510, fluid provided from the tube 510 to the tube 520 will generally be substantially free of water. Water can then exit from the tube 520 in a manner similar to the profile shown in FIG. 1 until substantially all water is removed from the sorbent tube 520. The water levels in both sorbent tubes 510 and 230 can be lowered to a desired level or substantially all water can be removed from both the sorbent tubes 510 and 520. While the receptacle 505 is shown as being sized and arranged to receive two sorbent tubes 510 and 520, the size can be altered such that more than two sorbent tubes can be placed into the receptacle 505. For example, the receptacle 505 can be configured to receive three sorbent tubes, four sorbent tubes, five sorbent tubes or more than five sorbent tubes in an in-line configuration similar to that shown in FIG. 5. Where the receptacle 505 is sized and arranged to receive multiple sorbent tubes, the receptacle 505 need not be filled with or occupied by the total number of sorbent tubes it is capable of receiving. For example, a receptacle sized and arranged to receive five sorbent tubes can be used to purge less than five sorbent tubes, e.g., one, two, three, or four two sorbent tubes, of water. While the device 500 is shown in a horizontal position in FIG. 5, it can be used in a vertical position with one of the sorbent tubes 510 and 520 resting against an end 506 or 508 of the receptacle 505, and the other sorbent tube can be in direct physical contact with the first sorbent tube. If desired, the sorbent tubes can be configured with bosses or spacers at the ends to provide a desired separation between the two sorbent tubes.

Figure 6:
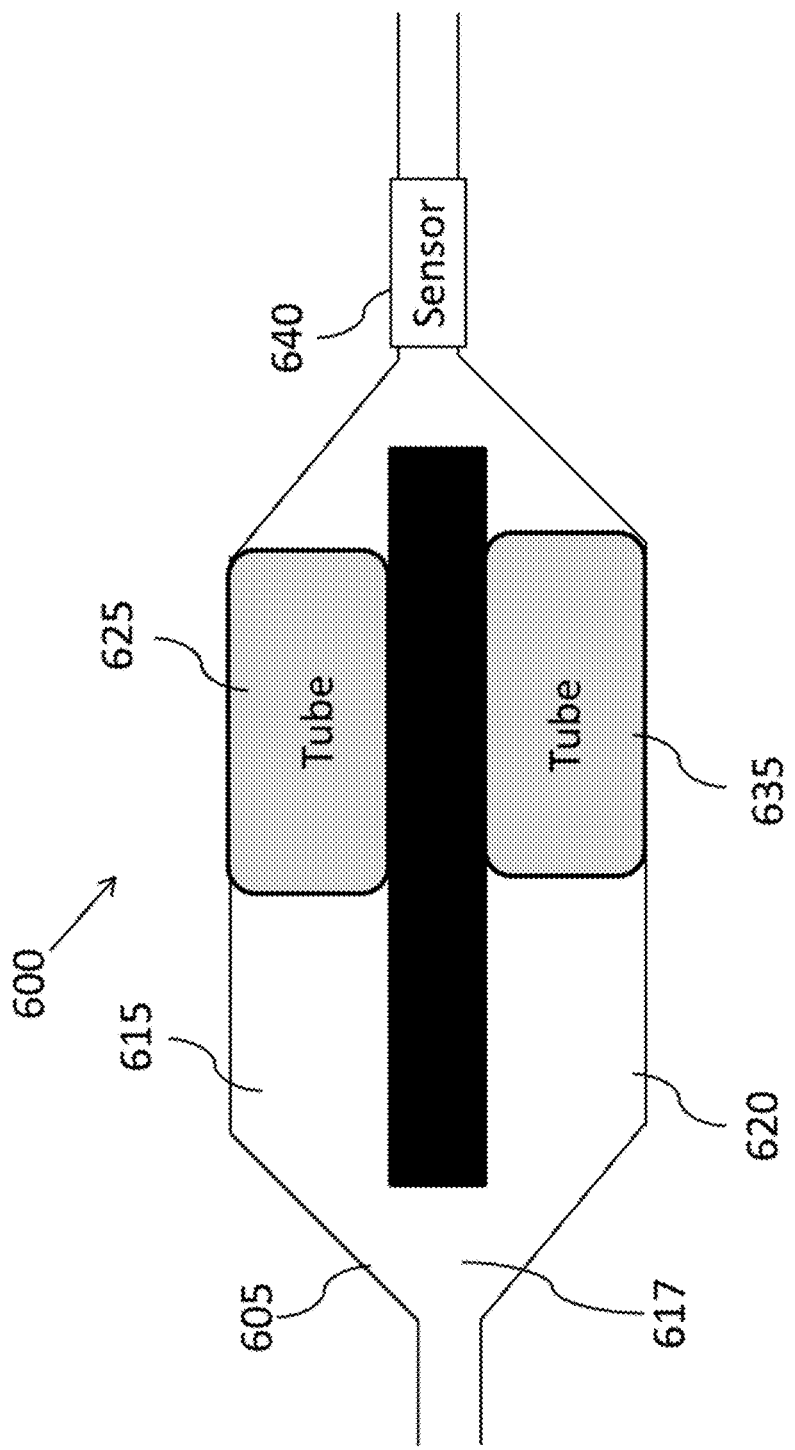
FIG. 6 is an illustration of a receptacle configured to receive two sorbent tubes in parallel, in accordance with certain examples.

In certain examples, two or more sorbent tubes can be placed in a common fluid flow path but not necessarily in-line. One illustration of stacked sorbent tubes is shown in FIG. 6. The device 600 comprises a receptacle 605 comprising a first compartment 615 configured to receive a sorbent tube 625 and a second compartment 620 configured to receive a sorbent tube 635. A common fluid flow path 617 is provided such that purging gas introduced into the receptacle 605 can be provided to both the sorbent tubes 625 and 635. A humidity sensor 640 is positioned at an end of the receptacle 605 where fluid exits from the receptacle 605. The humidity sensor 640 is operative to detect water levels in the exiting fluid. The device 600 can include a removable top or end so that the sorbent tubes 625 and 635 can be added to the compartments 615 and 620, respectively. While the sorbent tubes 625 and 635 are shown positioned toward one end of the receptacle 605, the sorbent tubes can be positioned anywhere within the compartments 615 and 620. Where the device 600 is oriented vertically with the humidity sensor 640 positioned at the base of the device 600, the sorbent tubes 625 and 635 may be positioned as shown in FIG. 6 due to gravity. In operation of the device 600, purging gas is provided to both sorbent tubes 625 and 635 simultaneously. Fluid exiting the sorbent tubes 625 and 635 is provided in combination to the humidity sensor 640, which is operative to detect water levels in the fluid. When the overall level of water reaches a desired level, the purging operation may be stopped and the sorbent tubes 625 and 635 can be removed for analysis, or where the purging is performed prior to exposure to analyte, the sorbent tubes 625 and 635 can be used to sample analyte. Devices configured with multiple compartments to hold more than two sorbent tubes can be constructed and used in a similar manner to the device 600. For example, a device comprising a common fluid flow path that is configured to receive, three, four, five or more sorbent tubes can be provided and used to purge each of the sorbent tubes in the device. Where a device comprising a plurality of compartments is available, a sorbent tube need not be present in every compartment for the device to work properly.

In certain embodiments, the devices described herein can include a humidity sensor for each compartment or sorbent tube to be purged. One illustration is shown in FIG. 7A. The device 700 comprises a first compartment 710 and a second compartment 715. A sorbent tube 720 is in the first compartment 710 and a sorbent tube 725 is in the second compartment 715. The first compartment 710 and the second compartment 715 may each include suitable internal positioners, bosses or fitting to position the sorbent tubes 720 and 725 at a desired position within the compartments 710 and 715, respectively. Alternatively, the compartments 710 and 715 may have a variable diameter so that the sorbent tubes 725 and 735 are placed in them and a friction fit is created between the sorbent tube and the wall of the compartment. A first humidity sensor 730 is fluidically coupled to the sorbent tube 720, and a second humidity sensor 735 is fluidically coupled to the sorbent tube 725. The humidity sensors 730 and 735 function independently of each other and each are electrically coupled to a processor, display, printer or other similar devices, which may be the same or different, e.g., one humidity sensor can be coupled to a display and the other humidity sensor can be coupled to printer. In some examples, each humidity sensor can be electrically coupled to its own processor, display, printer or the like. The humidity sensors 730 and 735 can include an address or be addressable so that the particular water level in a particular sorbent tube can be easily determined. In certain examples, the device 700 can include more than two compartments. For example, the device 700 can be configured with three or more compartments each configured to receive a single sorbent tube. Where more than two compartments are present, each compartment desirably is fluidically coupled to its own humidity sensor. In other examples, each compartment and/or associated humidity sensor can be individually addressed so that a user can identify which particular sorbent tube is associated with a displayed or detected water level.

In certain examples where two or more sorbent tubes that are each fluidically coupled to its own humidity sensor are present, the fluid flow path that provides purging gas may be separated so that no inter-sorbent tube contamination may occur. One such illustration is shown in FIG. 7B. The device 750 comprises two separated compartments 755 and 760 comprising a sorbent tube 765 and 770, respectively. Purging gas can be provided upstream to each of the compartments 755 and 760 such that no fluid flow path exists between the two compartments 755 and 760. By separating out the compartments 755 and 760, unwanted analyte transfer between sorbent tubes should not occur. The sorbent tube 765 is fluidically coupled to a humidity sensor 775, and the sorbent tube 770 is fluidically coupled to a humidity sensor 780. The humidity sensors 775 and 780 function independently of each other and each can be electrically coupled to a processor, display, printer or other similar devices, which may be the same or different. In some examples, each humidity sensor can be electrically coupled to its own processor, display, printer or the like. The humidity sensors 775 and 780 can include an address or be addressable so that the particular water level in a particular sorbent tube can be easily determined. In certain examples, the device 750 can include more than two compartments. For example, the device 750 can be configured with three or more compartments each configured to receive a single sorbent tube. Where more than two compartments are present, each compartment desirably is fluidically coupled to its own humidity sensor. In other examples, each compartment and/or associated humidity sensor can be individually addressed so that a user can identify which particular sorbent tube is associated with a displayed or detected water level.

In examples of the devices and systems where a processor is present, the processor can be any suitable commercially available processor. Similarly, numerous different types of humidity sensors, such as those commercially available from Honeywell Industries, can be used. If desired, the humidity sensor and/or processor can be selected from those able to withstand high temperatures commonly encountered in gas chromatographic (GC) techniques such that the sensor and/or processor can be integrated into the sorbent tube and not destroyed by the high temperatures. In other configurations, an inexpensive processor and/or sensor can be selected such that they are destroyed during the GC techniques from the high temperatures. In other configurations, the humidity sensor and/or processor may not be exposed to high temperatures and can be reused for additional sorbent tubes.

Figure 9:
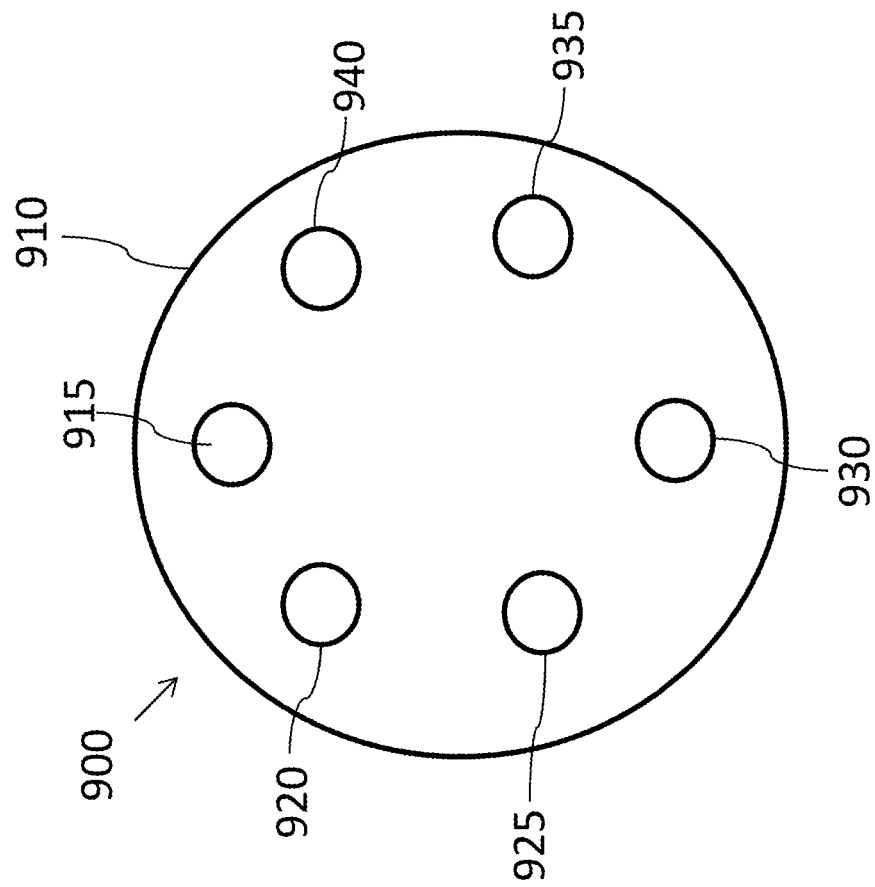
FIG. 9 is a top view of a device configured to receive six sorbent tubes for purging, in accordance with certain examples.
Figure 8:
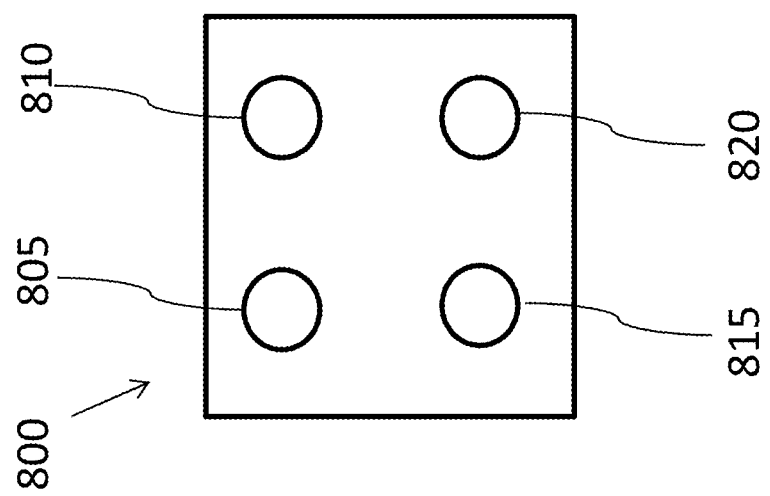
FIG. 8 is a top view of a device configured to receive four sorbent tubes for purging, in accordance with certain examples.

In certain embodiments where more than two compartments are present, the device can be configured in a block configuration, circular, e.g., in a carousel, or in other shapes and configurations. Referring to FIG. 8, a top view of a block configuration of a device 800 is shown which includes four compartments 805, 810, 815 and 820. Each of the compartments 805, 810, 815 and 820 is sized and arranged to receive at least one sorbent tube, though the exact dimensions of each compartment need not be exactly the same as the other compartments. In some examples, each of the compartments 805, 810, 815 and 820 is fluidically coupled to its own respective humidity sensor, whereas in other examples, fewer than four humidity sensors can be present in the device 800. For example, two humidity sensors can be present with one humidity sensor being configured to fluidically couple to the compartments 805 and 810 and the other humidity sensor being configured to fluidically couple to the compartments 815 and 820. In other embodiments, one or three humidity sensors can be used with the device 800. Each humidity sensor can be individually controlled so that the water level in each sorbent tube can be detected. The device 800 can couple to a manifold or coupler (not shown) that is configured to provide a purging gas to the compartments 805, 810, 815 and 820. Gaskets or sealing members can be included between the coupler and the device 800 so that a substantially fluid tight seal is provided between them. Referring to FIG. 9, a top view of a carousel configuration is shown. The device 900 comprises a housing 910 having a generally circular cross-section comprising a plurality of compartments 915, 920, 925, 930, 935 and 940 each configured to receive at least one sorbent tube (not shown). In some embodiments, each of the compartments 915, 920, 925, 930, 935 and 940 is fluidically coupled to its own respective humidity sensor, whereas in other examples, fewer than six humidity sensors can be present in the device 900, e.g., five, four, three, two or one humidity sensor can be present. Each humidity sensor present in the device 900 can be individually controlled so that the water level in each sorbent tube can be detected. The device 900 can couple to a manifold or coupler (not shown) that is configured to provide a purging gas to the compartments 915, 920, 925, 930, 935 and 940. Gaskets or sealing members can be included between the coupler and the device 900 so that a substantially fluid tight seal is provided between them.

Figure 10A:
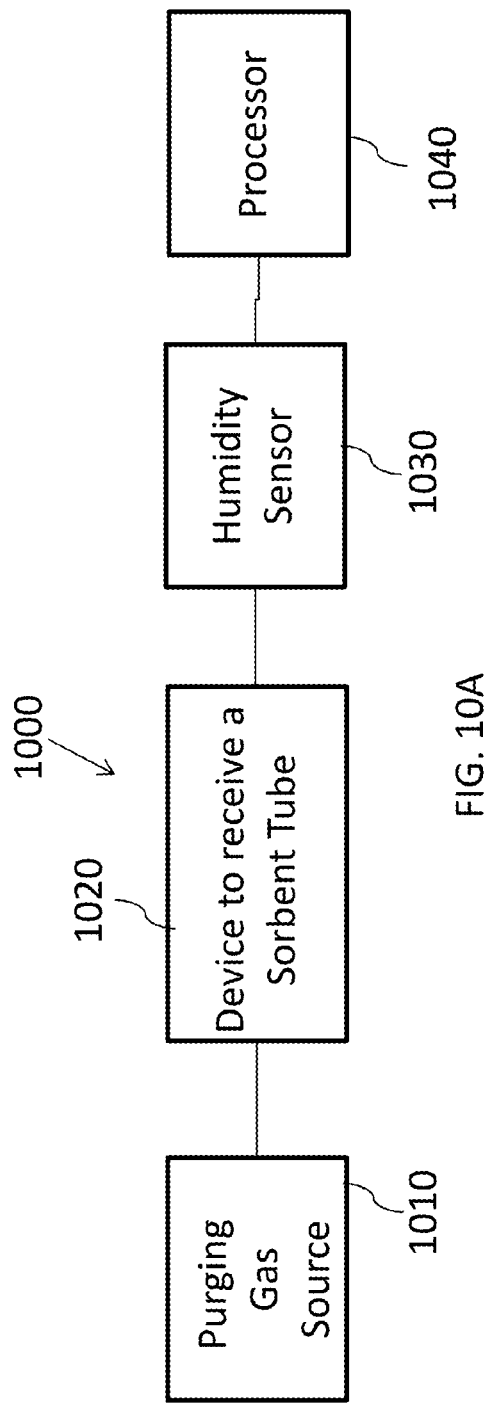
FIGS. 10A and 10B are block diagrams of systems comprising a purging gas source, a humidity sensor and a processor, in accordance with certain examples.

In certain examples, the devices described herein can be used in a system that comprises a purging gas and a processor. A block diagram of a system is shown in FIG. 10A. The system 1000 comprises a purging gas source 1010 fluidically coupled to a device 1020 configured to receive at least one sorbent tube, such as those illustrative devices described herein. The system 1000 also include a humidity sensor 1030 fluidically coupled to the device 1020. The humidity sensor 1030 is typically electrically coupled to a processor 1040, though it instead can be coupled to a display, printer, recorder or other devices designed to permit visualization or an indication of water levels detected by the humidity sensor 1030. In operation of the system 1000, purging gas is provided from the purging gas source 1010 to the device 1020 configured to receive at least one sorbent tube. Water levels in fluid exiting the device 1020 are detected by the humidity sensor 1030. The humidity sensor 1030 and optionally the purging gas source 1010 can be controlled with the processor 1040. For example, the processor 1040 can be configured to control provision of the purging gas to the device 1020 until a desired water level is detected by the humidity sensor 1030. The processor 1040 can then switch off a pump or valve to stop flow or purging gas to the device 1020. In some embodiments the processor 1040 can be part of a larger computer system operative to control the purging gas source 1010 and the humidity sensor 1030.

Figure 10B:
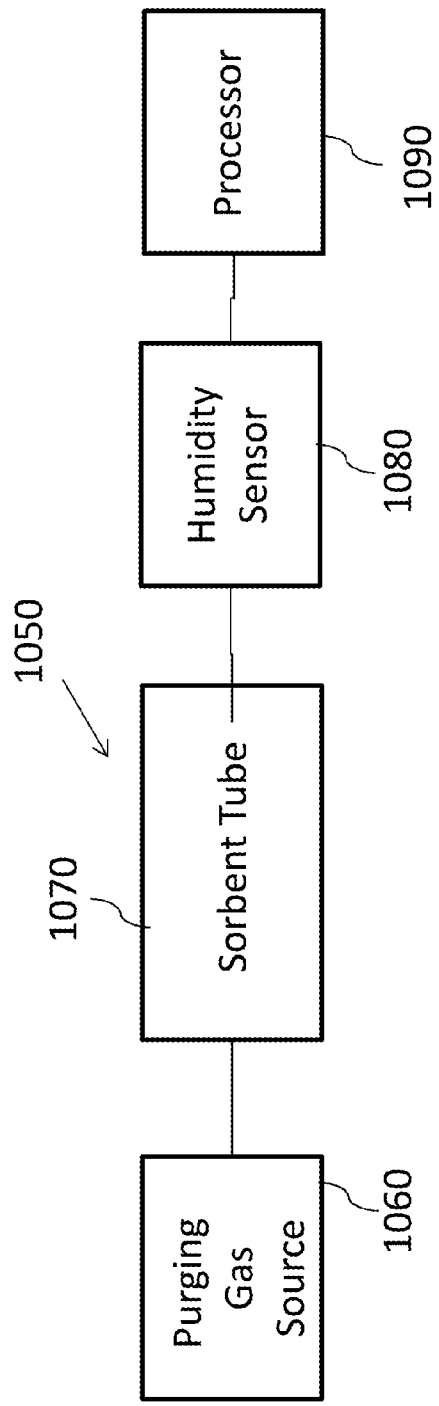

In certain embodiments, a sorbent tube can be directly coupled to a purging gas source and the device can be omitted. Referring to FIG. 10B, a system 1050 comprises a purging gas source 1060 fluidically coupled to a sorbent tube 1070. The sorbent tube 1070 is fluidically coupled to a humidity sensor 1080, which is electrically coupled to a processor 1090. In operation of the system 1050, purging gas is provided from the purging gas source 1060 to the sorbent device 1070. Water levels in fluid exiting the sorbent tube 1070 are detected by the humidity sensor 1080. The humidity sensor 1080 and optionally the purging gas source 1060 can be controlled with the processor 1090. For example, the processor 1090 can be configured to control provision of the purging gas to the sorbent tube 1070 until a desired water level is detected by the humidity sensor 1080. The processor 1090 can then switch off a pump or valve to stop flow or purging gas to the sorbent tube 1070. In some embodiments the processor 1090 can be part of a larger computer system operative to control the purging gas source 1060 and the humidity sensor 1080.

Figure 11:
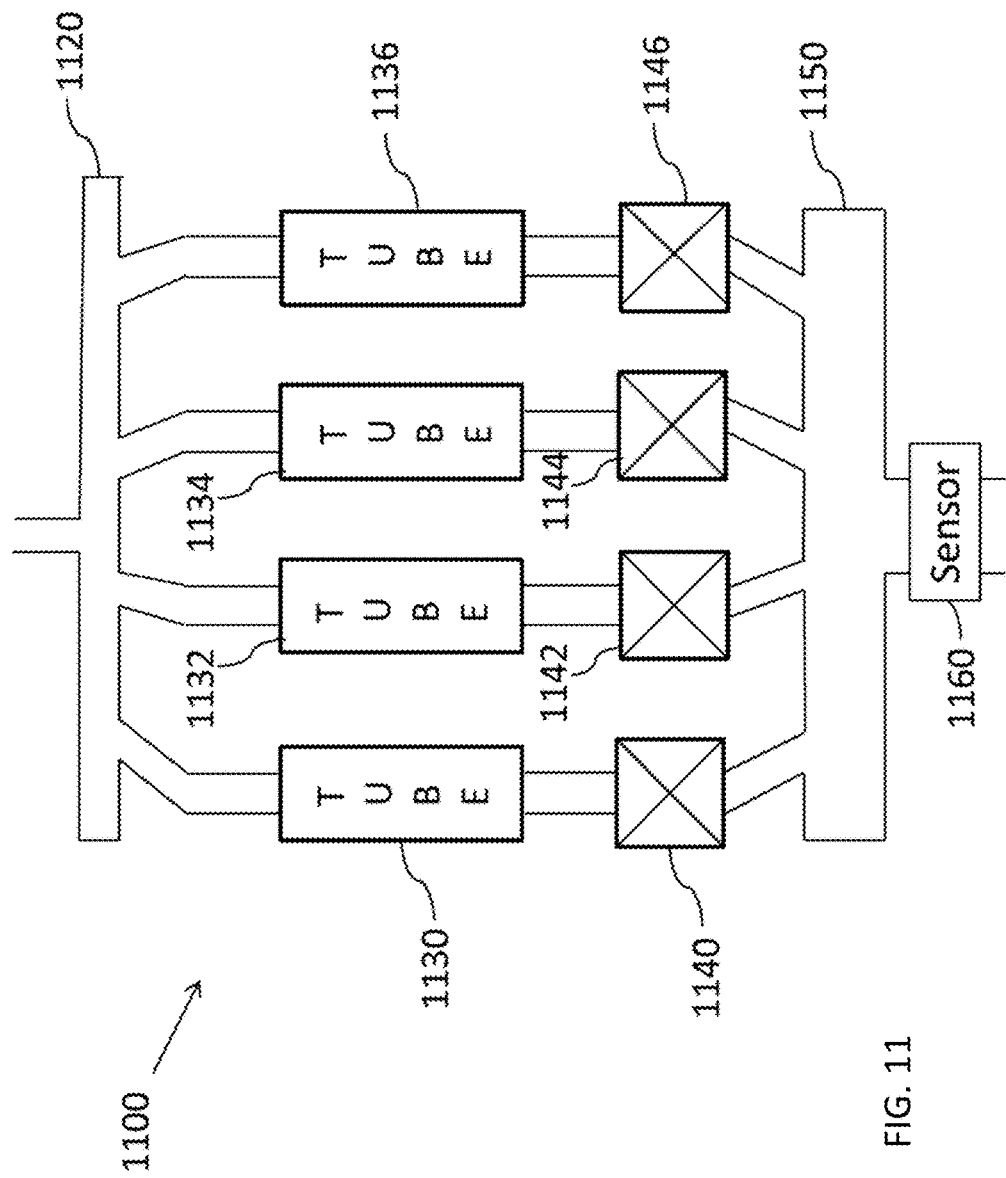
FIG. 11 is an illustration of a system comprising a single humidity sensor and a plurality of sorbent tubes, in accordance with certain examples.

In certain examples, a system comprising a single humidity sensor and configured to receive fluid flow from a plurality of sorbent tubes can be used to determine the water level in each of the sorbent tubes. Referring to FIG. 11, a system 1100 comprises a gas manifold 1120 fluidically coupled to a purging gas source (not shown). The gas manifold 1120 provides a purging gas to each of sorbent tubes 1130, 1132, 1134 and 1136. Each of the sorbent tubes 1130, 1132, 1134 and 1136 is fluidically coupled to a valve 1140, 1142, 1144 and 1146, respectively. The valves 1140, 1142, 1144 and 1146 can be independently actuated to open and closed positions such that fluid flow from a single sorbent tube (or multiple sorbent tubes) is provided to a humidity sensor 1160 through a gas manifold 1150. In some examples, only a single valve is open to the humidity sensor 1160 during any period, whereas in other examples, two, three or four of the valves 1140, 1142, 1144 and 1146 can be open to the humidity sensor 1160. The humidity sensor 1160 is typically coupled to a processor (not shown) that can receive signals from the humidity sensor 1160 to determine water levels in the fluid provided to the humidity sensor 1160. The valves 1140, 1142, 1144 and 1146 can be coupled to the same processor as the humidity sensor 1160 or can be coupled to a different processor. The processor can be configured to open one or more of the valves 1140, 1142, 1144 and 1146 to provide a desired fluid flow to the humidity sensor 1160. In certain examples, additional valves can be present between the gas manifold 1120 and the sorbent tubes 1130, 1132, 1134 and 1136 such that purging gas can be independently provided (or shut off) to any one or more of the sorbent tubes 1130, 1132, 1134 and 1136. Such additional valves can be integrated into the gas manifold 1120 or can be separate from it. Similarly, the valves 1140, 1142, 1144 and 1146 can be integrated into the gas manifold 1150 if desired. In some embodiments, the sorbent tubes 1130, 1132, 1134 and 1136 can be positioned in receptacles (not shown) that are between the gas manifold 1120 and the valves 1140, 1142, 1144 and 1146. As discussed herein, the receptacle can be configured to receive a single sorbent tube or two or more sorbent tubes, e.g., in series or in parallel, if desired. In certain examples, one or more temperature sensors (not shown) can be present in the system 1100 to account for the variations in the humidity levels based on the measured temperature.

Figure 12:
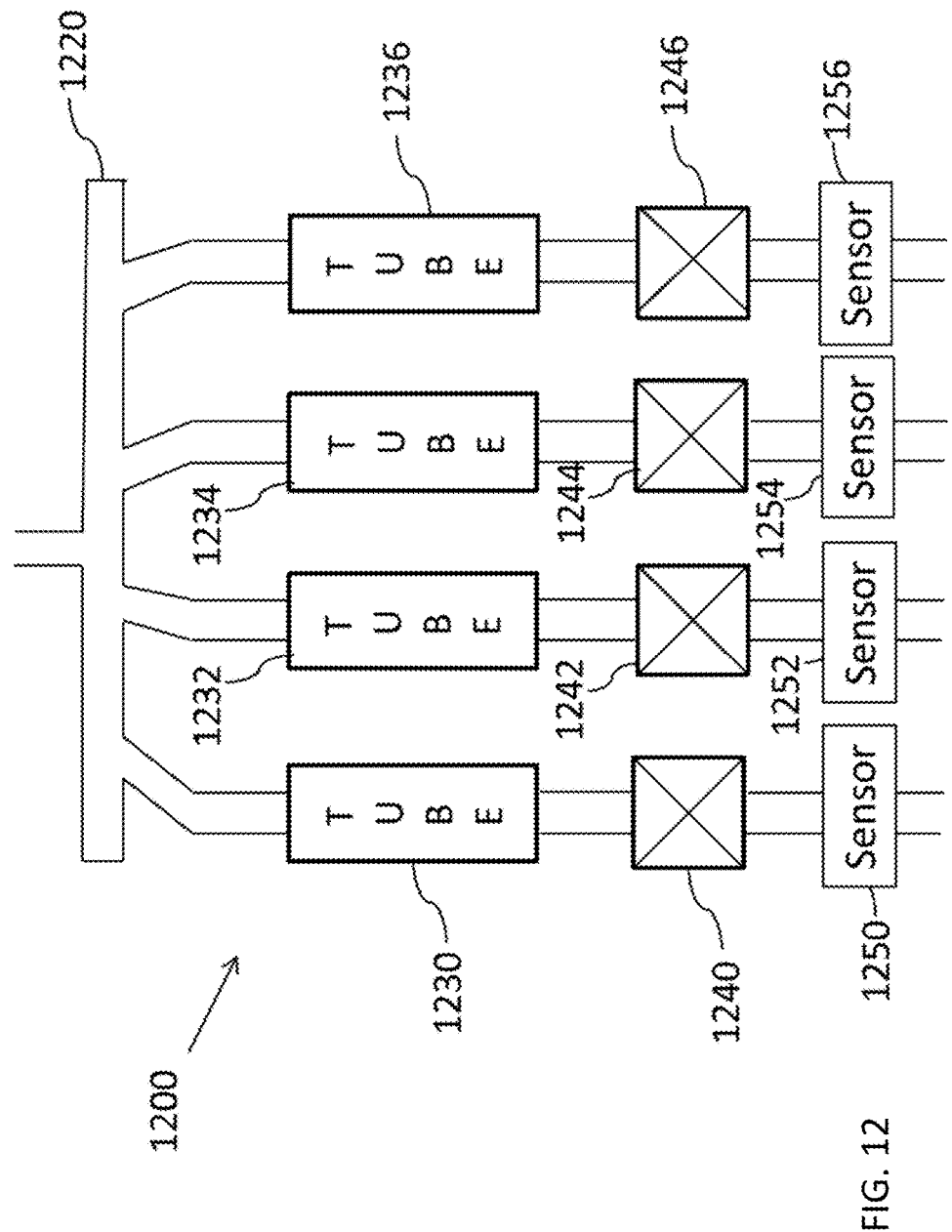
FIG. 12 is an illustration of a system comprising a plurality of humidity sensors and a plurality of sorbent tubes, in accordance with certain examples.

In some examples, a system that includes a humidity sensor for each respective sorbent tube can be used to detect water levels separately in each of the sorbent tubes. Referring to FIG. 12, a system 1200 comprises a gas manifold 1220 fluidically coupled to a purging gas source (not shown). The gas manifold 1220 provides a purging gas to each of sorbent tubes 1230, 1232, 1234 and 1236. Each of the sorbent tubes 1230, 1232, 1234 and 1236 is fluidically coupled to a valve 1240, 1242, 1244 and 1246, respectively. The valves 1240, 1242, 1244 and 1246 can be independently actuated to open and closed positions such that fluid flow from a single sorbent tube (or multiple sorbent tubes) is provided to a respective humidity sensor 1250, 1252, 1254 and 1256. In some examples, only a single valve is open to its respective humidity sensor during any period, whereas in other examples, two, three or four of the valves 1240, 1242, 1244 and 1246 can be open to its respective humidity sensor 1250, 1252, 1254 and 1256. The humidity sensors 1250, 1252, 1254 and 1256 are each typically coupled to a processor (not shown) that can receive signals from the humidity sensors 1250, 1252, 1254 and 1256 to determine water levels in the fluid provided to the humidity sensors 1250, 1252, 1254 and 1256. If desired, each of the humidity sensors 1250, 1252, 1254 and 1256 can be electrically coupled to its own dedicated processor. In some examples, the humidity sensors 1250, 1252, 1254 and 1256 and/or sorbent tubes 1230, 1232, 1234 and 1236 can be addressed or addressable such that the particular water level detected by the processor can be associated with a particular sorbent tube present in the system 1200. In some embodiments, the valves 1240, 1242, 1244 and 1246 can be coupled to the same processor as the humidity sensors 1250, 1252, 1254 and 1256 or can be coupled to a different processor. The processor can be configured to open one or more of the valves 1240, 1242, 1244 and 1246 to provide a desired fluid flow to the humidity sensors 1250, 1252, 1254 and 1256. In certain examples, additional valves can be present between the gas manifold 1220 and the sorbent tubes 1230, 1232, 1234 and 1236 such that purging gas can be independently provided (or shut off) to any one or more of the sorbent tubes 1230, 1232, 1234 and 1236. Such additional valves can be integrated into the gas manifold 1220 or can be separate from it. Similarly, the valves 1240, 1242, 1244 and 1246 can be integrated into a gas manifold (not shown) if desired. In some embodiments, the sorbent tubes 1230, 1232, 1234 and 1236 can be positioned in receptacles (not shown) that are between the gas manifold 1220 and the valves 1240, 1242, 1244 and 1246. As discussed herein, the receptacle can be configured to receive a single sorbent tube or two or more sorbent tubes, e.g., in series or in parallel, if desired. In certain examples, one or more temperature sensors (not shown) can be present in the system 1200 to account for the variations in the humidity levels based on the measured temperature.

Figure 13:
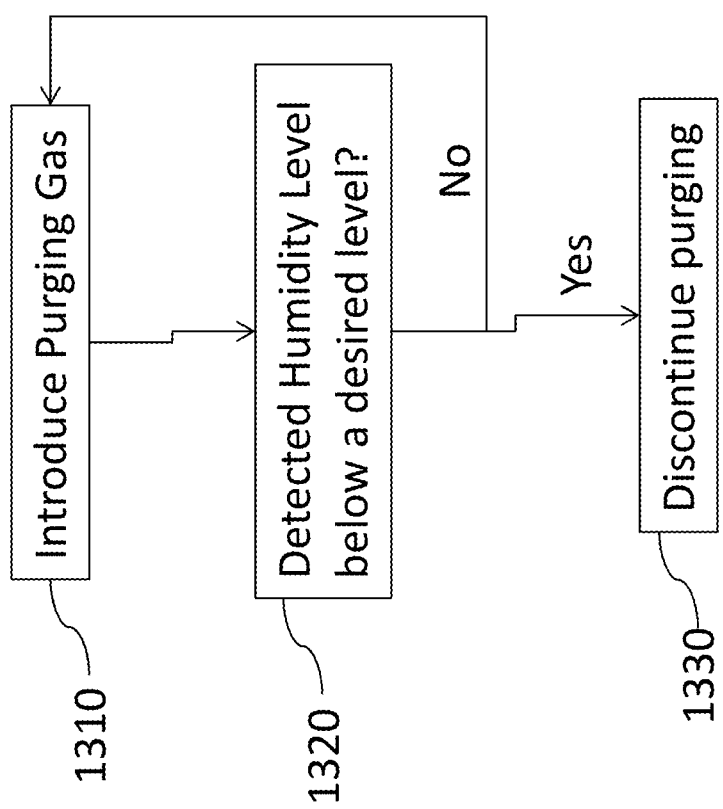
FIG. 13 is a block diagram of steps that can be used to purge a sorbent tube, in accordance with certain examples.

In certain embodiments, a method of purging a sorbent tube of water can be used to remove the water from a sorbent tube to a desired level. Referring to FIG. 13, the method can include introducing a purging gas into a sorbent tube at a step 1310 and detecting a humidity level at a step 1320. If the detected humidity level 1320 is below a selected level, then purging can be discontinued at a step 1330. If the detected humidity level is above a selected level, the purging gas can continue to be introduced into the sorbent tube at a step 1310 until a desired humidity level is reached and purging discontinued at step 1330. To increase overall accuracy of the detected humidity levels, a temperature can be detected and used to provide a correction factor for the humidity level. In some embodiments, introduction of the purging has during step 1310 can be continued as long as the humidity level changes by about 0.01% humidity per second or less. In certain examples, after detection of a humidity level change of about 0.1% humidity per second or more, the introduction of the purging gas can be discontinued at step 1330. In some examples, purging is not discontinued until after detection of a humidity level change of about 0.1% humidity per second or more followed by detection of a humidity level change of about 0.01% humidity per second. This plateau, decline, plateau phenomenon would be similar to that described in reference to FIG. 1 herein. In other examples, purging is not discontinued at step 1330 until a particular level of water is detected, e.g., about 3% relative humidity or less. While not shown in the process steps, the humidity sensor can be calibrated using fluid comprising a known amount of water so that a calibration curve can be constructed and used to determine the particular water level in fluid exiting a sorbent tube. Alternatively, the humidity sensor can be pre-calibrated so that its response is known and the user need not calibrate it prior to use.

In some embodiments, purging can be discontinued by switching off the purging gas source so that no additional gas is provided to the sorbent tube, whereas in other examples, a valve can be switched to a closed position so that no additional purging gas is provided to the sorbent tube. In other examples, a vent line can be opened such that purging gas flows out of the system and is not substantially provided to the sorbent tube. In certain examples, the humidity can be monitored continuously so that humidity levels are measured in real time from the beginning of introduction of a purging gas until a desired water level is reached. In other examples, the humidity can be monitored at discrete times, e.g., every 10 seconds, 20 seconds, 30 seconds, 1 minute or other selected intervals. In embodiments where a plurality of sorbent tubes are present and used with a single humidity sensor, it may be desirable to discretely monitor each sorbent tube and stagger the monitoring so that water levels in fluid from each tube can be detected with greater accuracy. Even where a plurality of humidity sensors are present, however, discrete monitoring can be performed if desired.

In certain embodiments, a method of facilitating removal of water from a sorbent tube comprises providing a humidity sensor configured to detect water levels in a fluid exiting the sorbent tube and provided to the humidity sensor. In some embodiments, the humidity sensor can be pre-configured with desired sampling times or other parameters such that a user couples the humidity sensor to a sorbent tube but need not otherwise configure it. In some instances, the method can include providing a valve configured to be placed between a purging gas source and the sorbent tube, the valve configured to permit flow of purging gas to the sorbent tube in one state and prevent flow of purging gas to the sorbent tube in another state. In certain examples, the method can include providing a processor configured to electrically couple to the humidity sensor. In some embodiments, the method can include providing a gas manifold configured to provide fluidic coupling between the sorbent tube and a purging gas source. If desired, a similar gas manifold can also be provided to couple the sorbent tube to one or more humidity sensors. In some embodiments, the method can include providing a receptacle configured to receive the sorbent tube and provide fluidic coupling between a purging gas source and the sorbent tube. In certain examples, a plurality of humidity sensors each configured to fluidically couple to a single sorbent tube to detect water levels in the fluidically coupled sorbent tube can be provided. In other examples, a plurality of receptacles each configured to receive at least one sorbent tube, in which each of the plurality of receptacles is fluidically coupled to one of the plurality of humidity sensors can be provided. If desired, a temperature sensor can be provided. Alternatively, the humidity sensor can be calibrated for measurements at a certain temperature or temperature range so that no temperature sensor need be present.

In some embodiments, the method can include providing an instrument configured to couple to the sorbent tube and to detect species eluting from the sorbent tube. In certain examples, the instrument can be a gas chromatograph or some other type of fluid chromatograph and may be hyphenated to one or more other instruments or detectors, e.g., the instrument can be a GC-MS. Suitable instruments for detecting species commonly adsorbed to sorbent tubes are commercially available from PerkinElmer Health Sciences, Inc. (Waltham, Mass.). In some configurations, the humidity sensor can be placed in-line with the instrument such that after removal of water analytical measurements can be initiated. In other configurations, water can be removed to a desired level and then the sorbent tube can be transferred to an instrument for detection of species adsorbed to the sorbent material in the sorbent tube. In some configurations, the sorbent tube can be in-line with the instrument, but water exiting the sorbent tube can be detected by the humidity sensor and vented from the system such that water is not provided to the chromatographic device or the detector. Once the water is removed to a desired level, the vent can be closed and sample exiting the sorbent tube can be provided to the chromatographic device or the detector. In certain instances, transfer of a purged sorbent tube to an instrument can be accomplished using autoloading techniques or autoloading devices so that little or no user intervention is required once the sorbent tubes are placed in a suitable device or system configured to purge them of water to a desired level.

In certain examples, the methods, systems and devices disclosed herein can be used to load sorbent tubes with a desired level of water. A loading curve would generally by the reverse of that shown in FIG. 1 with desired levels of water being detected in fluid exiting the sorbent tube and provided to a humidity sensor. A loading gas can be used and can include a certain level of water to provide a desired humidity level to the sorbent tube. This water level can be varied by mixing humidified gas with non-humidified gas prior to introduction into the sorbent tube. Where a plurality of sorbent tubes are loaded with water, each of the sorbent tubes need not be loaded to the same level and provision of the loading gas can be stopped once a particular sorbent tube reaches a desired water level.

In certain embodiments, a kit comprising a sorbent tube and a humidity sensor can be used to purge the sorbent tube or load the sorbent tube as desired. In some embodiments, the humidity sensor can be configured to detect water levels in fluid exiting the sorbent tube. In certain examples, the kit can include one or more of a temperature sensor, a gas manifold configured to couple the sorbent tube to a purging gas source, a receptacle configured to receive the sorbent tube, a plurality of receptacles each configured to receive at least one sorbent tube, a plurality of humidity sensors, a plurality of sorbent tubes, and/or instructions for using the humidity sensor or plurality of humidity sensors to purge the plurality of sorbent tubes of water.

The devices, systems and methods described herein can be used with many different types of sorbent tubes including, for example, those described in commonly owned U.S. patent application Ser. Nos. 12/573,048 and 12/729,432, the entire disclosure of each of which is hereby incorporated herein by reference. In brief, a sorbent tube generally includes a body comprising one, two or more sorbent materials positioned within the body in a suitable manner to adsorb species or analyte in a sample. For example, the sorbent tube can include a body comprising a sampling inlet, a sampling outlet and a cavity between the inlet and the outlet, the cavity comprising a serial arrangement of at least two different sorbent materials in which the sorbent materials are arranged from a material with a weakest sorbent strength to a material with a strongest sorbent strength with the weakest sorbent strength material adjacent to the sampling inlet. In certain examples, the body generally has dimensions of about ¼ inches wide by about 3.5-4 inches long.

Certain specific examples are described below to illustrate further some of the novel aspects of the technology described herein.

Example 1

Figure 14:
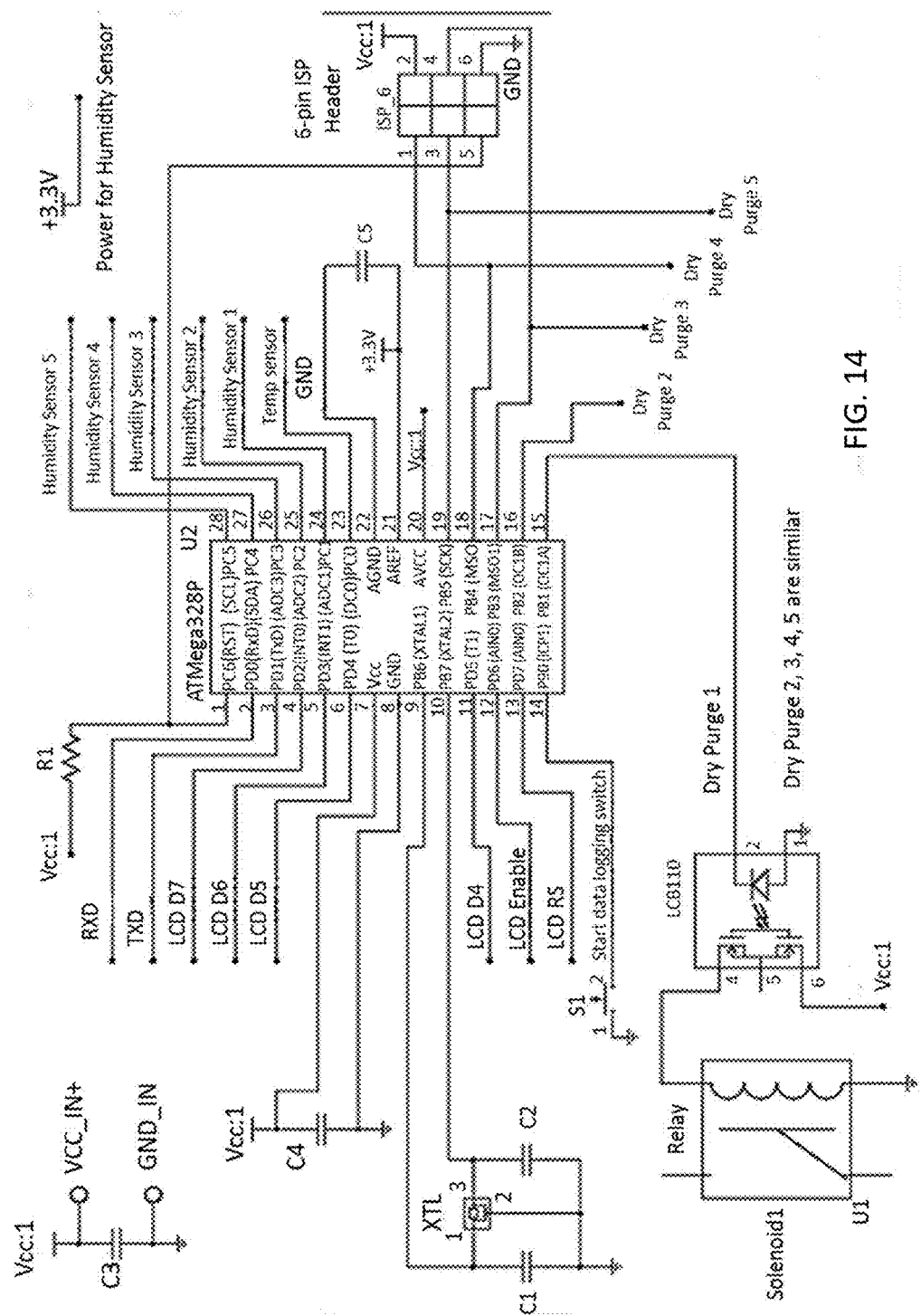
FIG. 14 is a circuit diagram of a system used to purge sorbent tubes, in accordance with certain examples.

A moisture sensor (HIH5031 commercially available from Honeywell) was interfaced to a microprocessor (Arduino Duemilanove commercially available from Arduino). The HIH5031 sensor uses 5V input and produces an output voltage that is proportional to the humidity. An Arduino microprocessor was used as it is low cost and easy to program/obtain. In addition, an Adafruit datalogging shield was used for real time timekeeping and recording of data to an SD data card. A circuit schematic of the system is shown in FIG. 14 showing the connections between the processor (ATMega328P) and the other components of the system.

Figure 15:
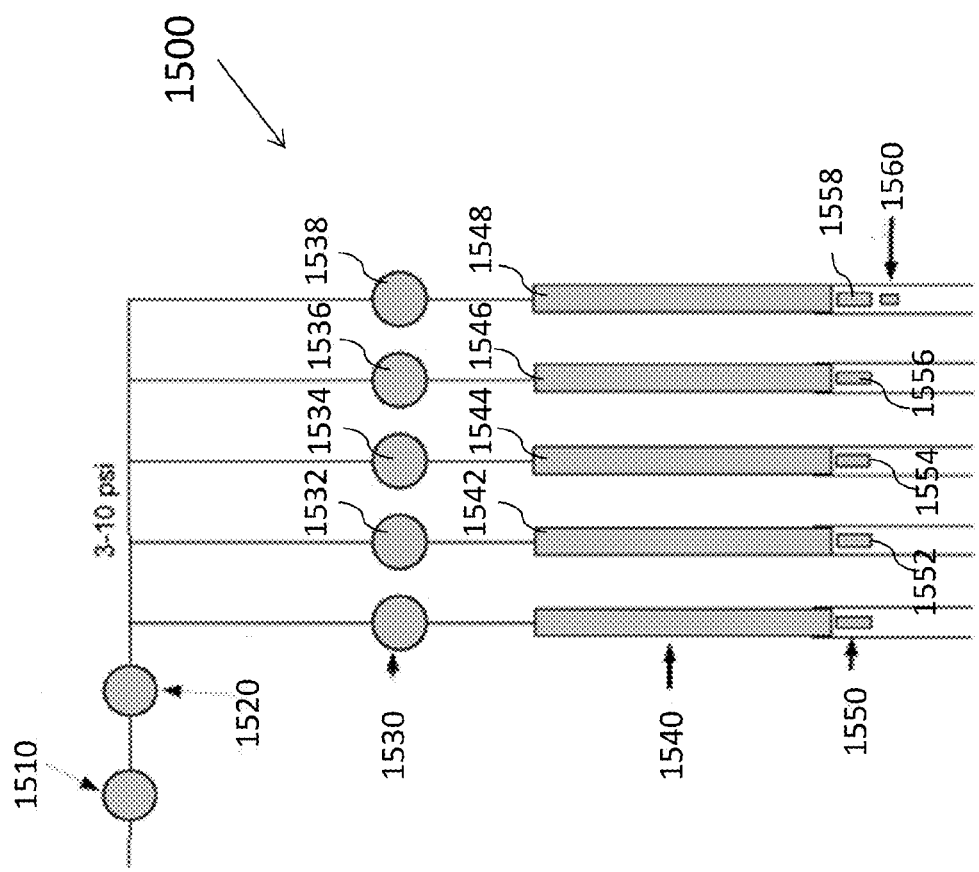
FIG. 15 is an illustration of a system used to purge sorbent tubes, in accordance with certain examples.

A soil vapor tube (SVI commercially available from PerkinElmer Health Sciences, Inc.) was purged with 6 Liters of clean nitrogen at 70% Relative Humidity. The tube was removed and it gained 35 mg of water when weighed on an analytical balance. The tube was attached to a dry purge apparatus as shown in FIG. 15. The system 1500 included a nitrogen pressure regulator 1510 fluidically coupled to a nitrogen gas source (not shown), a metering valve 1520, a plurality of solenoid valves 1530 1532, 1534, 1536 and 1538 each coupled to a respective sorbent tube 1540, 1542, 1544, 1546, and 1548. Suitable solenoid valves are commercially available from Clippard. Each of the sorbent tubes 1540, 1542, 1544, 1546, and 1548 was fluidically coupled to a humidity sensor 1550, 1552, 1554, 1556, and 1558 respectively, and the sorbent tube 1548 was also fluidically coupled to a temperature sensor 1560.

Figure 16:
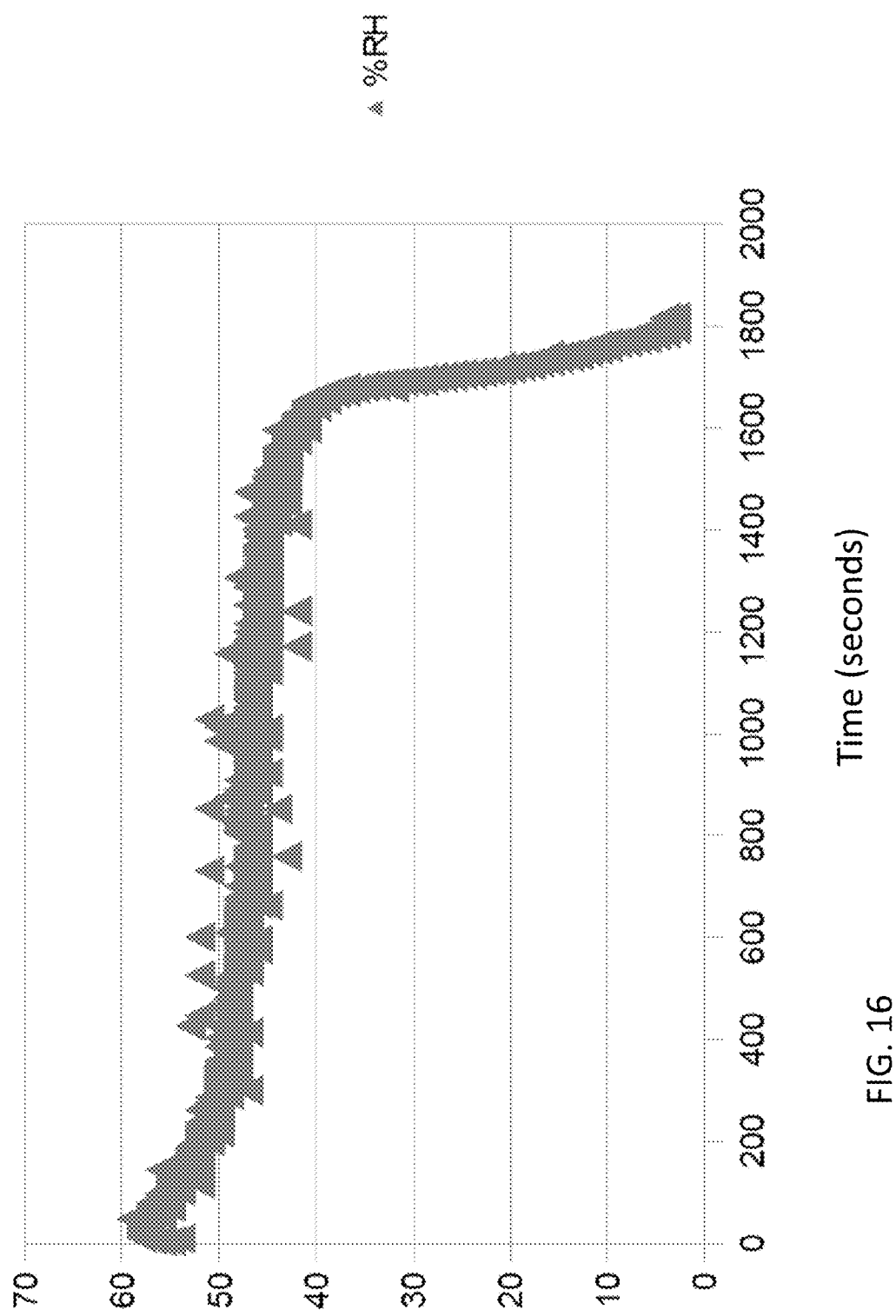
FIG. 16 is a graph of relative humidity versus time in seconds for a sorbent tube that included about 35 mg of water by weight, in accordance with certain examples.

The time/date/temperature and relative humidity of fluid exiting the sorbent tubes was recorded on a SD memory card. The system 1500 also can include an LCD (not shown) to visualize the data. The resulting data was plotted as shown in FIG. 16, which shows a graph of relative humidity versus time in seconds. Dry nitrogen was used as the purging gas, and a purge flow rate of 100 mL/minute was used.

Once the tube reaches 3% relative humidity (RH), the microprocessor can stop the flow of nitrogen to the sorbent tube by turning off its respective solenoid valve. If desired, this signal could also light a LED to signal the operator that the sorbent tube is ready or other visual indicia can be provided to notify a user that the desired water level has been reached.

A software program written to operate the system of FIG. 15 is provided below for convenience purposes only, and additional software programs suitable for controlling the system will be readily selected by the person of ordinary skill in the art, given the benefit of this disclosure.

When introducing elements of the aspects, embodiments and examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

```
/*
This program is to check the level of humidity in an air stream
using a HIH-5030 Honeywell humidity sensor.
Formula
VOUT=(VSUPPLY)(0.00636(sensor RH1) + 0.1515), typical at 25 C
Temperature correction
True RH1 = (Sensor RH1)/(1.0546-0.00216T), T in C
*/
// include the library code:
#include <LiquidCrystal.h>
#include <SdFat.h>
#include <Wire.h>
#include "RTClib.h"
// initialize the LCD library with the numbers of the interface pins
LiquidCrystal lcd(7, 6, 5, 4, 3, 2);
```

```
Serial.println();
#endif //ECHO_TO_SERIAL
if (file.writeError) error("write data");
delay(10);
//don't sync too often - requires 2048 bytes of I/O to SD card
if ((millis() - syncTime) < SYNC_INTERVAL) return;
syncTime = millis();
if (!file.sync()) error("sync");
delay(10);
}
delay(1000) //approx 1 second delay of cycle
}
```

```
#define LOG_INTERVAL 1000 // mills between entries
#define ECHO_TO_SERIAL 0 // echo data to serial port
#define WAIT_TO_START 0 // Wait for serial input in setup()
#define SYNC_INTERVAL 1000 // mills between calls to sync()
uint32_t syncTime = 0; // time of last sync()
RTC_DS1307 RTC; // define the Real Time Clock object
// The objects to talk to the SD card
Sd2Card card;
SdVolume volume;
SdFile root;
SdFile file;
//constants
const int AnalogTempSensor=0; // high accuracy LM35
const int AnalogHumidSensor1 =1 ; //humidity sensor connect to Analog pin 1
const int AnalogHumidSensor2 =2 ; //humidity sensor connect to Analog pin 2
const int AnalogHumidSensor3 =3 ; //humidity sensor connect to Analog pin 3
const int AnalogHumidSensor4 =4 ; //humidity sensor connect to Analog pin 4
const int AnalogHumidSensor5 =5 ; //humidity sensor connect to Analog pin 5
const int LogStartPin=8; //momentary contact switch
const int Solenoid1=9
const int Solenoid2=10
const int Solenoid3=11
const int Solenoid4=12
const int Solenoid5=13
//variables
float HumidSensorValue1=0;
float HumidSensorValue2=0;
float HumidSensorValue3=0;
float HumidSensorValue4=0;
float HumidSensorValue5=0;
//
```

```
float RH1=0;
float RH2=0;
float RH3=0;
float RH4=0;
float RH5=0;
int RH1Int=0 ; //Relative humidity as an int
int RH2Int=0 ; //Relative humidity as an int
int RH3Int=0 ; //Relative humidity as an int
int RH4Int=0 ; //Relative humidity as an int
int RH5Int=0 ; //Relative humidity as an int
float Voltage=3.34; //supply voltage for RH1 sensor
float RefVoltage=3.34; //ADC reference voltage
float Temperature=0;
int LogStart=0; //if 1 starts logging data to SD card
int LogStartButton=1; //if 0 indicated momentary contact switch is pressed
int HumidityLowLimit=3 //Humidity low setpoint to stop purge
void error(char *str)
{
Serial.print("error: ");
Serial.println(str);
while(1);
}
void setup(void)
{
pinMode(Solenoid1, OUTPUT);
pinMode(Solenoid2, OUTPUT);
pinMode(Solenoid3, OUTPUT);
pinMode(Solenoid4, OUTPUT);
pinMode(Solenoid5, OUTPUT);
digitalWrite(Solenoid1,HIGH);
digitalWrite(Solenoid2,HIGH);
```

```
digitalWrite(Solenoid3,HIGH);
digitalWrite(Solenoid4,HIGH);
digitalWrite(Solenoid5,HIGH);
lcd.begin(2, 40); // set up the LCD's number of rows and columns:
Serial.begin(9600);
Serial.println();
#if WAIT_TO_START
Serial.println("Type any character to start");
while (!Serial.available());
#endif //WAIT_TO_START
// initialize the SD card
if (!card.init()) error("card.init");
// initialize a FAT volume
if (!volume.init(card)) error("volume.init");
// open root directory
if (!root.openRoot(volume)) error("openRoot");
// create a new file
char name[] = "HUMIDY00.CSV";
for (uint8_t i = 0; i < 100; i++) {
name[6] = i/10 + '0';
name[7] = i%10 + '0';
if (file.open(root, name, O_CREAT | O_EXCL | O_WRITE)) break;
}
if (!file.isOpen()) error ("file.create");
Serial.print("Logging to: ");
Serial.println(name);
// write header
file.writeError = 0;
Wire.begin();
if (!RTC.begin()) {
file.println("RTC failed");
```

```
#if ECHO_TO_SERIAL
Serial.println("RTC failed");
#endif //ECHO_TO_SERIAL
}
file.println("seconds stamp datetime RH1Volt %RH1 RH2Volt %RH2 RH3Volt %RH3 RH4Volt %RH4 RH5Volt %RH5 Temp");
#if ECHO_TO_SERIAL
Serial.println("seconds stamp datetime RH1Volt %RH1 RH2Volt %RH2 RH3Volt %RH3 RH4Volt %RH4 RH5Volt %RH5 Temp");
#endif //ECHO_TO_SERIAL
// attempt to write out the header to the file
if (file.writeError || !file.sync()) {
error("write header");
}
// If you want to set the aref to something other than 5v
analogReference(EXTERNAL);
digitalWrite(LogStartPin, HIGH); //turn on pullup resistors
// following line sets the RTC to the date & time this sketch was compiled
// RTC.adjust(DateTime(__DATE__, __TIME__));
}
void loop(void)
{
lcd.clear();
lcd.setCursor(0,0);
lcd.print("Humidity Meter ");
//check log start button
LogStartButton=digitalRead (LogStartPin);
if (LogStartButton==0)
{
if (LogStart==0)
LogStart=1;
```

```
else
LogStart=0;
}
if (LogStart==1)
lcd.print("LOG");
//check humidity sensor reading
HumidSensorValue1 = analogRead(AnalogHumidSensor1); // humidity sensor reading
HumidSensorValue1=HumidSensorValue1/1024.0*RefVoltage;
HumidSensorValue2 = analogRead(AnalogHumidSensor2); // humidity sensor reading
HumidSensorValue2=HumidSensorValue2/1024.0*RefVoltage;
HumidSensorValue3 = analogRead(AnalogHumidSensor3); // humidity sensor reading
HumidSensorValue3=HumidSensorValue3/1024.0*RefVoltage;
HumidSensorValue4 = analogRead(AnalogHumidSensor4); // humidity sensor reading
HumidSensorValue4=HumidSensorValue4/1024.0*RefVoltage;
HumidSensorValue5 = analogRead(AnalogHumidSensor5); // humidity sensor reading
HumidSensorValue5=HumidSensorValue5/1024.0*RefVoltage;
// check temperature section
Temperature=analogRead(AnalogTempSensor);
Temperature=Temperature*RefVoltage*100/1024;
RH1 =(((HumidSensorValue1/Voltage)-0.1515)/0.00636);  //converting voltage to Sensor %RH1
RH1 = (RH1)/(1.0546-0.00216*Temperature); //temperature correction
RH1Int = RH1;
if (RH1Int <= HumidityLowLimit) {digitalWrite(Solenoid1.LOW}
RH2 =(((HumidSensorValue2/Voltage)-0.1515)/0.00636);  //converting voltage to Sensor %RH2
RH2 = (RH2)/(1.0546-0.00216*Temperature); //temperature correction
RH2Int = RH2;
if (RH2Int <= HumidityLowLimit) {digitalWrite(Solenoid2.LOW}
RH3 =(((HumidSensorValue3/Voltage)-0.1515)/0.00636);  //converting voltage to Sensor %RH3
```

RH3 = (RH3)/(1.0546-0.00216*Temperature); //temperature correction

RH3Int = RH3;

if (RH3Int <= HumidityLowLimit) {digitalWrite(Solenoid3.LOW}

RH4 =(((HumidSensorValue4/Voltage)-0.1515)/0.00636); //converting voltage to Sensor %RH4

RH4 = (RH4)/(1.0546-0.00216*Temperature); //temperature correction

RH4Int = RH4;

if (RH4Int <= HumidityLowLimit) {digitalWrite(Solenoid4.LOW}

RH5 =(((HumidSensorValue5/Voltage)-0.1515)/0.00636); //converting voltage to Sensor %RH5

RH5 = (RH5)/(1.0546-0.00216*Temperature); //temperature correction

RH5Int = RH5;

if (RH5Int <= HumidityLowLimit) {digitalWrite(Solenoid5.LOW}

//display section lcd.print(" Temp ");

lcd.print(Temperature);

lcd.print(millis()/1000);

lcd.print (" sec");

lcd.setCursor(0,1);

//lcd.print("Sensor ");

//lcd.print(HumidSensorValue1);

//lcd.print(" V ");

lcd.print(RH1Int);

lcd.print(" RH1 ");

lcd.print(RH2Int);

lcd.print(" RH2 ");

lcd.print(RH3Int);

lcd.print(" RH3 ");

lcd.print(RH4Int);

lcd.print(" RH4 ");

lcd.print(RH5Int);

```
lcd.print(" RH5 ");
DateTime now;
// clear print error
file.writeError = 0;
// delay for the amount of time we want between readings
delay((LOG_INTERVAL -1) - (millis() % LOG_INTERVAL));
if (LogStart==1)
{
// log seconds since starting
uint32_t m = millis();
file.print(m/1000); // seconds since start
file.print(" ");
// fetch the time
now = RTC.now();
// log time
file.print(now.unixtime()); // seconds since 1/1/1970
file.print(" ");
file.print("");
file.print(now.year(), DEC);
file.print("/");
file.print(now.month(), DEC);
file.print("/");
file.print(now.day(), DEC);
file.print(" ");
file.print(now.hour(), DEC);
file.print(":");
file.print(now.minute(), DEC);
file.print(":");
file.print(now.second(), DEC);
file.print("");
file.print(" ");
```

```
file.print(HumidSensorValue1);
file.print(" ");
file.print(RH1Int);
file.print(" ");
file.print(HumidSensorValue2);
file.print(" ");
file.print(RH2Int);
file.print(" ");
file.print(HumidSensorValue3);
file.print(" ");
file.print(RH3Int);
file.print(" ");
file.print(HumidSensorValue4);
file.print(" ");
file.print(RH4Int);
file.print(" ");
file.print(HumidSensorValue5);
file.print(" ");
file.print(RH5Int);
file.print(" ");
file.print(Temperature);
file.println();
#if ECHO_TO_SERIAL
Serial.print(m/1000); // seconds since start
Serial.print(" ");
Serial.print(now.unixtime()); // seconds since 1/1/1970
Serial.print(" ");
Serial.print("");
Serial.print(now.year(), DEC);
Serial.print("/");
Serial.print(now.month(), DEC);
```

```
Serial.print("/");
Serial.print(now.day(), DEC);
Serial.print(" ");
Serial.print(now.hour(), DEC);
Serial.print(":");
Serial.print(now.minute(), DEC);
Serial.print(":");
Serial.print(now.second(), DEC);
Serial.print("");
Serial.print(" ");
Serial.print(HumidSensorValue1);
Serial.print(" ");
Serial.print(RH1Int);
Serial.print(" ");
Serial.print(HumidSensorValue2);
Serial.print(" ");
Serial.print(RH2Int);
Serial.print(" ");
Serial.print(HumidSensorValue3);
Serial.print(" ");
Serial.print(RH3Int);
Serial.print(" ");
Serial.print(HumidSensorValue4);
Serial.print(" ");
Serial.print(RH4Int);
Serial.print(" ");
Serial.print(HumidSensorValue5);
Serial.print(" ");
Serial.print(RH5Int);
Serial.print(" ");
Serial.print(Temperature);
```

The invention claimed is:

1. A device configured to load a sorbent tube with a desired level of water using a fluid flow comprising humidified fluid, the device comprising a humidity sensor constructed and arranged to fluidically couple to the sorbent tube, the humidity sensor separate from the sorbent tube and configured to receive a fluid stream from the sorbent tube to determine the level of water in the sorbent tube, and a processor electrically coupled to the humidity sensor, the processor configured to permit the fluid flow comprising the humidified fluid into the sorbent tube when the determined level of water in the sorbent tube is below a desired level and to stop the fluid flow into the sorbent tube when the determined level of water in the sorbent tube reaches a desired level, in which the humidity sensor is configured to detect an inflection point as an indicator of the desired level of water in the sorbent tube and wherein the desired level of water in the sorbent tube is measured by the humidity sensor to be about 3% relative humidity when the fluid flow into the sorbent tube is stopped by the processor.

2. The device of claim 1, in which the device comprising the humidity sensor is configured to receive the sorbent tube.

3. The device of claim 1, in which the device comprising the humidity sensor is configured to fluidically couple to a receptacle comprising the sorbent tube, wherein the receptacle comprising the sorbent tube is separate from the device comprising the humidity sensor.

4. The device of claim 1, further comprising a plurality of receptacles each configured to receive a single sorbent tube.

5. The device of claim 4, further comprising a plurality of humidity sensors in which a respective one of the plurality of receptacles is fluidically coupled to one of the plurality of humidity sensors and is separate from the plurality of humidity sensors and in which each of the plurality of humidity sensors is electrically coupled to the processor.

6. The device of claim 1, further comprising a temperature sensor.

7. A system comprising:
a humidified gas source;
a receptacle configured to receive at least one sorbent tube and fluidically coupled to the humidified gas source;
a humidity sensor separate from the receptacle and fluidically coupled to the receptacle and configured to receive fluid from the receptacle to detect water levels in the received fluid;
a processor electrically coupled to the humidity sensor and configured to permit fluid flow from the humidified gas source into the at least one sorbent tube when water levels in the at least one sorbent tube detected by the humidity sensor are below a desired level and to stop fluid flow from the humidified gas source into the at least one sorbent tube when water levels in the at least one sorbent tube detected by the humidity sensor are at a desired level;
a manifold fluidically coupled to the humidified gas source, the manifold comprising at least one outlet configured to fluidically couple to the receptacle;
a valve in the manifold and electrically coupled to the processor, the valve being configured to actuate between a closed position to stop the fluid flow from the humidified gas source into the at least one sorbent tube and an open position to permit the fluid flow from the humidified gas source into the at least one sorbent tube, in which the processor is configured to actuate the valve from the open position to the closed position when the water level in the at least one sorbent tube is measured by the humidity sensor to be about 3% relative humidity.

8. The system of claim 7, in which the humidified gas source is coupled to a plurality of receptacles each configured to receive at least one sorbent tube.

9. The system of claim 7, in which the receptacle is configured to receive two separate sorbent tubes positioned in parallel.

10. The system of claim 7, in which the receptacle is configured to receive two separate sorbent tubes positioned in series.

11. The system of claim 7, in which the manifold comprises at least two ports and each of the at least two ports of the manifold is also fluidically coupled to a single sorbent tube.

12. The system of claim 11, further comprising a plurality of humidity sensors each configured to fluidically couple to a respective single sorbent tube.

13. The system of claim 12, further comprising a respective valve in each of the at least two ports of the manifold, in which each respective valve is electrically coupled to the processor, in which each valve is independently configured to actuate between an open position to permit the fluid flow from the humidified gas source into a respective single sorbent tube when the detected water level in the single sorbent tube is below the desired level and a closed position to stop the fluid flow from the humidified gas source into the respective single sorbent tube when the detected water level in the single sorbent tube reaches the desired level.

14. The system of claim 13, further comprising a temperature sensor electrically coupled to the processor.

15. A device configured to load a sorbent tube with a desired level of water using a fluid flow comprising humidified fluid, the device comprising a humidity sensor fluidically coupled to the sorbent tube, the humidity sensor separate from the sorbent tube and configured to receive a fluid stream from the sorbent tube to determine the level of water in the sorbent tube, and a processor electrically coupled to the humidity sensor, the processor configured to permit the fluid flow comprising the humidified fluid into the sorbent tube when the determined level of water in the sorbent tube is below a desired level and to stop the fluid flow into the sorbent tube when the determined level of water in the sorbent tube reaches a desired level, in which the sorbent tube comprises at least two different sorbent materials arranged from a material with a weakest sorbent strength to a material with a strongest sorbent strength with the weakest sorbent strength material adjacent to a sampling inlet of the sorbent tube.

16. The device of claim 15, further comprising at least one temperature sensor coupled to the processor.

* * * * *